US006699478B1

(12) United States Patent
Hancock et al.

(10) Patent No.: US 6,699,478 B1
(45) Date of Patent: Mar. 2, 2004

(54) ENHANCED IMMUNE RESPONSE TO ATTACHMENT (G) PROTEIN OF RESPIRATORY SYNCYTIAL VIRUS

(75) Inventors: Gerald E. Hancock, Honeoye Falls, NY (US); Paul W. Tebbey, Rochester, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 0 days.

(21) Appl. No.: 09/526,195

(22) Filed: Mar. 15, 2000

Related U.S. Application Data

(63) Continuation-in-part of application No. PCT/US98/19656, filed on Sep. 17, 1998.
(60) Provisional application No. 60/084,863, filed on May 8, 1998, and provisional application No. 60/059,684, filed on Sep. 19, 1997.

(51) Int. Cl.[7] .................... A61K 39/155; A61K 39/295; A61K 39/12; C12N 7/01; C07K 7/00; C07K 17/00

(52) U.S. Cl. ................................ 424/211.1; 424/202.1; 424/204.1; 424/186.1; 435/235.1; 530/300; 530/350

(58) Field of Search ............................... 424/9.2, 204.1, 424/186.1, 211.1, 202.1; 435/5, 235.1; 530/300, 350; 930/10, 220

(56) References Cited

FOREIGN PATENT DOCUMENTS

| | | |
|---|---|---|
| WO | WO 96/14418 | 5/1996 |
| WO | WO 97/46581 | 12/1997 |

OTHER PUBLICATIONS

Power et al. Virology, Apr. 14, 1997; 230:155–166.*

Hancock et al. Journal of Virology. 1996; 70 (11): 7783–7791.*

Hancock, et al., "Generation of Atypical Pulmonary Inflammatory Responses in BALB/c Mice after Immunization with the Native Attachment (G) Glycoprotein of Respiratory Syncytial Virus," *J. Virol.*, 70 (11) : 7783–7791 (1996).

Waris, et al., "Priming with Live Respiratory Syncytial Virus (RSV) Prevents the Enhanced Pulmonary Inflammatory Response Seen after RSV Challenge in BALB/c Mice Immunized with Formalin–Inactivated RSV," *J. Virol.*, 71 (9) : 6935–6939 (1997).

Cane, Patricia A., "Analysis of Linear Epitopes Recognised by the Primary Human Antibody Response to a Variable Region of the Attachment (G) Protein of Respiratory Syncytial Virus," *Journal of Medical Virology*, 51: 297–304 (1997).

Sparer, et al., "Eliminating a Region of Respiratory Syncytial Virus Attachment Protein Allows Induction of Protective Immunity without Vaccine–enhanced Lung Eosinophilia," *J. Exp. Med.*, 187 (11) : 1921–1926 (1998).

Tebbey, et al., "Atypical Pulmonary Eosinophilia Is Mediated by a Specific Amino Acid Sequence of the Attachment (G) Protein of Respiratory Syncytial Virus," *J. Exp. Med.*, 188 (10) : 1967–1972 (1998).

Kim, et al., "Respiratory Syncytial Virus Disease in Infants Despite Prior Administration of Antigenic Inactivated Vaccine," *American Journal of Epidemiology*, 89 (4) : 422–434 (1969).

Kim, et al., "Cell–mediated Immunity to Respiratory Syncytial Virus Induced by Inactivated Vaccine or by Infection," *Pediat. Res.*, 10 (1) : 75–78 (1976).

Rammensee, et al., "MHC ligands and peptide motifs: first listing," *Immunogenetics*, 41 (4) : 178–228 (1995).

Satake, et al., "Respiratory syncytial virus envelope glycoprotein (G) has a novel structure," *Nucleic Acids Research*, 13 (21): 7795–7812 (1985).

Wertz, et al., "Nucleotide sequence of the G protein gene of human respiratory syncytial virus reveals an unusual type of viral membrane protein," *Proc. Natl. Acad. Sci. USA*, 82: 4075–4079 (1985).

Srikiatkhachorn, et al., "Induction of Th–1 and Th–2 Responses by Respiratory Syncytial Virus Attachment Glycoprotein Is Epitope and Major Histocompatibility Complex Independent," *J. Virol.*, 73 (8) : 6590–6597 (1999).

Tebbey, et al., "Characterization of Immune Responses to the Attachment (G) Protein of Respiratory Syncytial Virus in Inbred Mice," 10th International Conference on Negative Strand Viruses (Abstract No. A152); Sep. 21, 1997.

Tebbey, et al., "Characterization of Immune Responses to the Attachment (G) Protein of Respiratory Syncytial Virus in Inbred Mice," 10th International Conference on Negative Strand Viruses (poster presentation given Sep. 24, 1997).

* cited by examiner

*Primary Examiner*—James Housel
*Assistant Examiner*—Shanon Foley
(74) *Attorney, Agent, or Firm*—J. Darrell Fontenot

(57) ABSTRACT

An altered G protein or portion thereof of RSV which retains immunogenicity and which, when incorporated into an immunogenic composition or vaccine and administered to a vertebrate, does not induce enhanced disease (e.g., atypical pulmonary inflammation such as pulmonary eosinophilia) upon subsequent infection with RSV, is disclosed. In a particular embodiment, the altered G protein comprises an alteration in one or more regions selected from the group consisting of the region from amino acid 159 to amino acid 198, the region from amino acid 159 to amino acid 174, the region from amino acid 171 to amino acid 187, the region from amino acid 176 to amino acid 190, and the region from amino acid 184 to amino acid 198 of the RSV G protein. Immunogenic compositions and vaccines comprising the altered RSV G protein, and optionally comprising RSV F protein, are also disclosed.

19 Claims, 15 Drawing Sheets

| Peptide | Amino Acids | Sequence | |
|---|---|---|---|
| 1 | 48-62 | MIISTSLIIAAIIFI | SEQ ID NO: 1 |
| 2 | 56-70 | IAAIIFIASANHKVT | SEQ ID NO: 2 |
| 3 | 64-78 | SANHKVTPTTAIIQD | SEQ ID NO: 3 |
| 4 | 72-86 | TTAIIQDATSQIKNT | SEQ ID NO: 4 |
| 5 | 80-94 | TSQIKNTTPTYLTQN | SEQ ID NO: 5 |
| 6 | 88-102 | PTYLTQNPQLGISPS | SEQ ID NO: 6 |
| 7 | 95-110 | PQLGISPSNPSEITSQ | SEQ ID NO: 7 |
| 8 | 104-118 | PSEITSQITTILAST | SEQ ID NO: 8 |
| 9 | 112-126 | TTILASTTPGVKSTL | SEQ ID NO: 9 |
| 10 | 120-134 | PGVKSTLQSTTVKTK | SEQ ID NO: 10 |
| 11 | 128-142 | STTVKTKNTTTTQTQ | SEQ ID NO: 11 |
| 12 | 136-150 | TTTTQTQPSKPTTKQ | SEQ ID NO: 12 |
| 13 | 144-158 | SKPTTKQRQNKPPSK | SEQ ID NO: 13 |
| 14 | 151-166 | RQNKPPSKPNNDFHFE | SEQ ID NO: 14 |
| 15 | 159-174 | PNNDFHFEVFNFVPCS | SEQ ID NO: 15 |
| 16 | 168-181 | FNFVPCSICSNNPT | SEQ ID NO: 16 |
| 17 | 171-187 | VPCSICSNNPTCWAICK | SEQ ID NO: 17 |
| 18 | 176-190 | CSNNPTCWAICKRIP | SEQ ID NO: 18 |
| 19 | 184-198 | AICKRIPNKKPGKKT | SEQ ID NO: 19 |
| 20 | 192-206 | KKPGKKTTTKPTKKP | SEQ ID NO: 20 |
| 21 | 200-214 | TKPTKKPTLKTTKKD | SEQ ID NO: 21 |
| 22 | 208-222 | LKTTKKDPKPQTTKS | SEQ ID NO: 22 |
| 23 | 216-230 | KPQTTKSKEVPTTKP | SEQ ID NO: 23 |
| 24 | 224-238 | EVPTTKPTEEPTINT | SEQ ID NO: 24 |
| 25 | 232-246 | EEPTINTTKTNIITT | SEQ ID NO: 25 |
| 26 | 240-254 | KTNIITTLLTSNTTG | SEQ ID NO: 26 |
| 27 | 248-262 | LTSNTTGNPELTSQM | SEQ ID NO: 27 |
| 28 | 256-270 | PELTSQMETFHSTSS | SEQ ID NO: 28 |
| 29 | 264-278 | TFHSTSSEGNPSPSQ | SEQ ID NO: 29 |
| 30 | 272-286 | GNPSPSQVSTTSEYP | SEQ ID NO: 30 |
| 31 | 280-294 | STTSEYPSQPSSPPN | SEQ ID NO: 31 |

Figure 2

| Vaccine | Antibody Treatment | % CD4+ Cells | % CD8+ Cells | % BAL Eosinophils |
|---|---|---|---|---|
| G/Stimulon™ QS-21 | rat Ig | 21.2 | 8.5 | 67.2 ± 8.5 |
| G/Stimulon™ QS-21 | anti-CD4 | 1.5 | 15.0 | 8.1 ± 4.7** |
| G/Stimulon™ QS-21 | anti-CD8 | 24.4 | 2.7 | 63.8 ± 6.4 |
| Peptide 19-KLH/Stimulon™ QS-21 | rat Ig | 19.0 | 7.7 | 29.6 ± 13.3 |
| Peptide 19-KLH/Stimulon™ QS-21 | anti-CD4 | 0.3 | 20.0 | 0.75 ± 0.6** |
| Peptide 19-KLH/Stimulon™ QS-21 | anti-CD8 | 27.4 | 2.8 | 32.8 ± 10.3 |
| RSV | none | 25.8 | 11.2 | 0.7 ±1.0 |

Figure 8

SEQUENCE LISTING

```
<160> NUMBER OF SEQ ID NOS:  37

<210> SEQ ID NO 1
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 1

Met Ile Ile Ser Thr Ser Leu Ile Ile Ala Ala Ile Ile Phe Ile
 1               5                  10                  15


<210> SEQ ID NO 2
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 2

Ile Ala Ala Ile Ile Phe Ile Ala Ser Ala Asn His Lys Val Thr
 1               5                  10                  15


<210> SEQ ID NO 3
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 3

Ser Ala Asn His Lys Val Thr Pro Thr Thr Ala Ile Ile Gln Asp
 1               5                  10                  15


<210> SEQ ID NO 4
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 4

Thr Thr Ala Ile Ile Gln Asp Ala Thr Ser Gln Ile Lys Asn Thr
 1               5                  10                  15


<210> SEQ ID NO 5
```

-continued

<211> LENGTH: 15
<212> TYPE: PRT
<213> ORGANISM: Artificial Sequence
<220> FEATURE:
<223> OTHER INFORMATION: Synthetic Peptide

<400> SEQUENCE: 5

Thr Ser Gln Ile Lys Asn Thr Thr Pro Thr Tyr Leu Thr Gln Asn
 1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 6

Pro Thr Tyr Leu Thr Gln Asn Pro Gln Leu Gly Ile Ser Pro Ser
 1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 7

Pro Gln Leu Gly Ile Ser Pro Ser Asn Pro Ser Glu Ile Thr Ser Gln
 1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 8

Pro Ser Glu Ile Thr Ser Gln Ile Thr Thr Ile Leu Ala Ser Thr
 1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 9

Thr Thr Ile Leu Ala Ser Thr Thr Pro Gly Val Lys Ser Thr Leu
 1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 10

Pro Gly Val Lys Ser Thr Leu Gln Ser Thr Thr Val Lys Thr Lys
 1               5                   10                  15

<210> SEQ ID NO 11
<211> LENGTH: 15

-continued

```
<212> TYPE: PRT
<213> ORGANISM: Artificial Sequence
<220> FEATURE:
<223> OTHER INFORMATION: Synthetic Peptide

<400> SEQUENCE: 11

Ser Thr Thr Val Lys Thr Lys Asn Thr Thr Thr Thr Gln Thr Gln
 1               5                   10                  15


<210> SEQ ID NO 12
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 12

Thr Thr Thr Thr Gln Thr Gln Pro Ser Lys Pro Thr Thr Lys Gln
 1               5                   10                  15


<210> SEQ ID NO 13
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 13

Ser Lys Pro Thr Thr Lys Gln Arg Gln Asn Lys Pro Pro Ser Lys
 1               5                   10                  15


<210> SEQ ID NO 14
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 14

Arg Gln Asn Lys Pro Pro Ser Lys Pro Asn Asn Asp Phe His Phe Glu
 1               5                   10                  15


<210> SEQ ID NO 15
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 15

Pro Asn Asn Asp Phe His Phe Glu Val Phe Asn Phe Val Pro Cys Ser
 1               5                   10                  15


<210> SEQ ID NO 16
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 16

Phe Asn Phe Val Pro Cys Ser Ile Cys Ser Asn Asn Pro Thr
 1               5                   10


<210> SEQ ID NO 17
<211> LENGTH: 17
<212> TYPE: PRT
```

-continued

```
<213> ORGANISM: Artificial Sequence
<220> FEATURE:
<223> OTHER INFORMATION: Synthetic Peptide

<400> SEQUENCE: 17

Val Pro Cys Ser Ile Cys Ser Asn Asn Pro Thr Cys Trp Ala Ile Cys
 1               5                  10                  15

Lys


<210> SEQ ID NO 18
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 18

Cys Ser Asn Asn Pro Thr Cys Trp Ala Ile Cys Lys Arg Ile Pro
 1               5                  10                  15


<210> SEQ ID NO 19
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 19

Ala Ile Cys Lys Arg Ile Pro Asn Lys Lys Pro Gly Lys Lys Thr
 1               5                  10                  15


<210> SEQ ID NO 20
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 20

Lys Lys Pro Gly Lys Lys Thr Thr Thr Lys Pro Thr Lys Lys Pro
 1               5                  10                  15


<210> SEQ ID NO 21
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 21

Thr Lys Pro Thr Lys Lys Pro Thr Leu Lys Thr Thr Lys Lys Asp
 1               5                  10                  15


<210> SEQ ID NO 22
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 22

Leu Lys Thr Thr Lys Lys Asp Pro Lys Pro Gln Thr Thr Lys Ser
 1               5                  10                  15


<210> SEQ ID NO 23
<211> LENGTH: 15
```

-continued

<212> TYPE: PRT
<213> ORGANISM: Artificial Sequence
<220> FEATURE:
<223> OTHER INFORMATION: Synthetic Peptide

<400> SEQUENCE: 23

Lys Pro Gln Thr Thr Lys Ser Lys Glu Val Pro Thr Thr Lys Pro
1 5 10 15

<210> SEQ ID NO 24
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 24

Glu Val Pro Thr Thr Lys Pro Thr Glu Glu Pro Thr Ile Asn Thr
1 5 10 15

<210> SEQ ID NO 25
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 25

Glu Glu Pro Thr Ile Asn Thr Thr Lys Thr Asn Ile Ile Thr Thr
1 5 10 15

<210> SEQ ID NO 26
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 26

Lys Thr Asn Ile Ile Thr Thr Leu Leu Thr Ser Asn Thr Thr Gly
1 5 10 15

<210> SEQ ID NO 27
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 27

Leu Thr Ser Asn Thr Thr Gly Asn Pro Glu Leu Thr Ser Gln Met
1 5 10 15

<210> SEQ ID NO 28
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 28

Pro Glu Leu Thr Ser Gln Met Glu Thr Phe His Ser Thr Ser Ser
1 5 10 15

<210> SEQ ID NO 29
<211> LENGTH: 15
<212> TYPE: PRT

-continued

<213> ORGANISM: Artificial Sequence
<220> FEATURE:
<223> OTHER INFORMATION: Synthetic Peptide

<400> SEQUENCE: 29

Thr Phe His Ser Thr Ser Ser Glu Gly Asn Pro Ser Pro Ser Gln
1 5 10 15

<210> SEQ ID NO 30
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 30

Gly Asn Pro Ser Pro Ser Gln Val Ser Thr Thr Ser Glu Tyr Pro
1 5 10 15

<210> SEQ ID NO 31
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 31

Ser Thr Thr Ser Glu Tyr Pro Ser Gln Pro Ser Ser Pro Pro Asn
1 5 10 15

<210> SEQ ID NO 32
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 32

Ala Ile Cys Gly Arg Gly Pro Asn Gly Lys Pro Gly Lys Lys Thr
1 5 10 15

<210> SEQ ID NO 33
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 33

Ala Gly Cys Gly Arg Gly Pro Gly Gly Lys Pro Gly Lys Gly Thr
1 5 10 15

<210> SEQ ID NO 34
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 34

Ala Ile Cys Gly Arg Gly Pro Asn Lys Lys Pro Gly Lys Lys Thr
1 5 10 15

<210> SEQ ID NO 35
<211> LENGTH: 15
<212> TYPE: PRT
<213> ORGANISM: Artificial Sequence -continued

```
<220> FEATURE:
<223> OTHER INFORMATION: Synthetic Peptide

<400> SEQUENCE: 35

Ala Ile Cys Gly Arg Ile Pro Asn Lys Lys Pro Gly Lys Lys Thr
 1              5                   10                  15


<210> SEQ ID NO 36
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 36

Ala Gly Cys Lys Arg Ile Pro Asn Lys Lys Pro Gly Lys Lys Thr
 1              5                   10                  15


<210> SEQ ID NO 37
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 37

Ala Gly Cys Lys Arg Ile Pro Asn Lys Gly Pro Gly Lys Lys Thr
 1              5                   10                  15
```

ENHANCED IMMUNE RESPONSE TO ATTACHMENT (G) PROTEIN OF RESPIRATORY SYNCYTIAL VIRUS

RELATED APPLICATIONS

This application is a continuation-in part of International Application No. PCT/US98/19656, filed Sep. 17, 1998, which designates the United States, and which claims the benefit of U.S. Provisional Application No. 60/059,684, filed Sep. 19, 1997, and U.S. Provisional Application No. 60/084,863, filed May 8, 1998, the contents of all of which are incorporated herein by reference in their entirety.

BACKGROUND OF THE INVENTION

Respiratory Syncytial Virus (RSV), a negative strand virus of the paramyxoviridae family, is a major cause of lower pulmonary tract disease, particularly in young children and infants. The parenteral administration of formalin-inactivated RSV (FI-RSV) as a vaccine has been associated with enhanced disease in RSV-naive recipients (seronegative) who subsequently became infected with wild-type RSV. The enhanced disease was characterized by an increased proportion of eosinophils in both the peripheral blood and lungs of affected individuals (Kim et al., *Am. J. Epidemiol.* 89:422–434 (1969); Kim et al., *Pediatric Res.* 10:75–78 (1976)). Recent studies in rodents have indicated that FI-RSV induces a T-helper 2 (TH2) immune response, whereas live attenuated viral vaccine are preferentially associated with T-helper 1 (TH 1) responses.

RSV contains two prominent outer envelope glycoproteins, fusion (F) protein and attachment (G) protein, that are important for viral infectivity and thus serve as reasonable targets for the design of a subunit vaccine to RSV. It has previously been shown that the generation of neutralizing antibodies to RSV by an F-protein-based vaccine can be greatly increased by the inclusion of G protein (Hancock et al., *J. Virol.* 70:7783–7791 (1996)). However, in attempting to understand the molecular basis for FI-RSV-induced enhanced disease, it has previously been shown that the native attachment (G) glycoprotein of RSV is sufficient to prime for atypical pulmonary inflammation characterized by pulmonary eosinophilia associated with high production levels of Interleukin-5 (IL-5), a TH2 cytokine (Hancock et al., *J. Virol.* 70:7783–7791 (1996)). In fact, the in vivo depletion of IL-5 significantly reduces the eosinophilic response in bronchoalveolar lavage cells of G protein-immunized mice challenged with RSV. The response to G protein was shown to be T cell mediated by transfer of G protein-specific CD4+ T cell lines into naive recipient mice, resulting in atypical pulmonary inflammatory responses upon subsequent challenge (Alwan et al., *J. Exp. Med.* 179:81–89 (1994)).

SUMMARY OF THE INVENTION

The immune responses elicited by native RSV G protein and a series of overlapping peptides (shown in FIG. 2) extending from amino acids 48 to 294 of G protein have been characterized as described herein. In stimulation assays of splenocytes from G protein-vaccinated mice, one peptide (19, spanning amino acids 184–198) was dominant in its ability to stimulate spleen cell proliferation in BALB/c mice (FIG. 3). In these mice, in the absence of any similar effect from other G protein-derived peptides, the use of peptide 19 as an antigen resulted in a stimulation of spleen cell proliferation that was 15-fold above background levels. Peptide 19 was also found to be the major region of the G protein involved in cytokine release, as both IFN-γ and IL-5 were detected in the induction of supernatants from cultures of splenocytes derived from G protein-vaccinated BALB/c mice (FIGS. 4A and 4B). Peptide 19 (amino acids 184–198 of the RSV G protein) specifically induces pulmonary eosinophilia in BALB/c mice. Mice vaccinated with peptide 19 conjugated to keyhole limpet hemocyanin (KLH) showed significant pulmonary eosinophilia (39.5% of total bronchoalveolar lavage cells) upon subsequent challenge with live RSV (FIG. 5). In contrast, mice immunized with a peptide containing amino acids 208–222 (peptide 22) conjugated to KLH exhibited minimal pulmonary eosinophilia (3.3%). Mutations in the amino acid sequence of peptide 19 abrogated the ability to predispose mice for pulmonary eosinophilia (FIG. 6). Furthermore, in additional mouse strains utilized as described herein, peptides 15 (amino acids 159–174), 17 (amino acids 171–187) and 18 (amino acids 176–190) also showed significant ability to induce proliferative responses of G protein-primed splenocytes (FIGS. 11A–11C).

The in vivo depletion of CD4+ cells abrogated pulmonary eosinophilia in mice vaccinated with the peptide 19 conjugate, whereas the depletion of CD8+ cells had a negligible effect (FIG. 8). These data indicate an association between peptide 19 of RSV G protein and the CD4+ T cell-mediated induction of pulmonary eosinophilia in response to live RSV challenge, suggesting that peptide 19-specific CD4+ T cells are the causative agent of pulmonary eosinophilia. In analyzing human peripheral blood cells from 43 donors, 6 showed reactivity to RSV G protein, 3 of which responded to peptide 19 (FIG. 7). This data suggests that peptide 19 may be involved in the onset of bronchiolitis, atopy or asthma that is sometimes observed following RSV infection of seronegative infants (Welliver and Welliver, *Pediatrics in Review* 14:134–139 (1993)). Taken together, these data indicate that the region of RSV G protein spanning amino acids 159–198 has the capacity to prime vertebrates for pulmonary eosinophilia and thus may mediate enhanced disease upon subsequent infection of the vertebrate with RSV.

Accordingly, the invention pertains to an altered G protein or polypeptide of RSV which retains immunogenicity and which, when incorporated into an immunogenic composition or vaccine and administered to a vertebrate, provides protection without inducing enhanced disease upon subsequent infection of the vertebrate with RSV. In a particular embodiment, the enhanced disease is atypical pulmonary inflammation, particularly pulmonary eosinophilia. In one embodiment, the alteration is in the region from amino acid 184 to amino acid 198 of the RSV G protein. In another embodiment, the alteration is in a region selected from the group consisting of the region from amino acid 159 to amino acid 198 of the RSV G protein, the region from amino acid 159 to amino acid 174 of the RSV G protein, the region from amino acid 171 to amino acid 187 of the RSV G protein, and the region from amino acid 176 to amino acid 190 of the RSV G protein. In an alternate embodiment, the alteration results in inhibition of priming for IL-5 secretion by the altered G protein or polypeptide relative to wild type G protein. In another embodiment, the alteration results in enhancement of priming for IFN-γ secretion by the altered G protein or polypeptide relative to wild type G protein.

The invention also pertains to a nucleic acid molecule encoding an altered G protein or polypeptide of RSV, where the altered protein or polypeptide retains immunogenicity and, when incorporated into an immunogenic composition or vaccine and administered to a vertebrate, does not induce enhanced disease upon subsequent infection of the vertebrate with RSV. In one embodiment, the alteration is in the region from amino acid 184 to amino acid 198 of the RSV G protein. In another embodiment, the alteration is in a region selected from the group consisting of the region from amino acid 159 to amino acid 198 of the RSV G protein, the region from amino acid 159 to amino acid 174 of the RSV G protein, the region from amino acid 171 to amino acid 187 of the RSV G protein, and the region from amino acid 176 to amino acid 190 of the RSV G protein.

The invention also encompasses DNA constructs comprising a nucleic acid molecule described herein operably linked to a regulatory sequence. In a particular embodiment, the invention pertains to a chimeric DNA construct comprising: (a) a nucleic acid molecule encoding an altered G protein or polypeptide of RSV, where the altered protein or polypeptide retains immunogenicity and, when incorporated into an immunogenic composition or vaccine and administered to a vertebrate, does not induce enhanced disease upon subsequent infection of the vertebrate with RSV; (b) a nucleic acid molecule encoding all or an immunogenic portion of F protein of RSV; and (c) a regulatory sequence operably linked to both the F and altered G proteins.

The invention also relates to a recombinant host cell comprising a DNA construct described herein, as well as to a method of producing an altered G protein or polypeptide of RSV which retains immunogenicity and which, when incorporated into an immunogenic composition or vaccine and administered to a vertebrate, does not induce enhanced disease upon subsequent infection of the vertebrate with RSV, comprising maintaining a recombinant host cell of the invention under conditions suitable for expression of the altered G protein or polypeptide.

The invention also pertains to a method of producing a chimeric polypeptide comprising an altered G protein or polypeptide of RSV which retains immunogenicity and which, when incorporated into an immunogenic composition or vaccine and administered to a vertebrate, does not induce enhanced disease upon subsequent infection of the vertebrate with RSV, and all or an immunogenic portion of F protein of RSV.

The invention also pertains to the use of the altered G protein or polypeptide, or recombinant host cell for expression thereof, for the manufacture of a medicament, such as a vaccine.

The invention further relates to an immunogenic composition comprising a physiologically acceptable medium and an altered G protein or polypeptide of RSV which retains immunogenicity and which, when incorporated into an immunogenic composition and administered to a vertebrate, does not induce enhanced disease upon subsequent infection of the vertebrate with RSV. In a particular embodiment, the immunogenic composition results in inhibition of priming for IL-5 secretion relative to an immunogenic composition comprising wild type G protein. In another embodiment, the immunogenic composition results in enhancement of priming for IFN-γ secretion relative to an immunogenic composition comprising wild type G protein. In one embodiment, the alteration is in the region from amino acid 184 to amino acid 198 of the RSV G protein. In another embodiment, the alteration is in a region selected from the group consisting of the region from amino acid 159 to amino acid 198 of the RSV G protein, the region from amino acid 159 to amino acid 174 of the RSV G protein, the region from amino acid 171 to amino acid 187 of the RSV G protein, and the region from amino acid 176 to amino acid 190 of the RSV G protein. The immunogenic composition can also comprise all or a portion of RSV F protein.

The invention also pertains to a vaccine composition comprising an immunologically effective amount of altered G protein or polypeptide of RSV which retains immunogenicity and which, when incorporated into a vaccine and administered to a vertebrate, provides protection without inducing enhanced disease upon subsequent infection of the vertebrate with RSV. In one embodiment, the alteration is in the region from amino acid 184 to amino acid 198. In another embodiment, the alteration is in a region selected from the group consisting of the region from amino acid 159 to amino acid 198 of the RSV G protein, the region from amino acid 159 to amino acid 174 of the RSV G protein, the region from amino acid 171 to amino acid 187 of the RSV G protein, and the region from amino acid 176 to amino acid 190 of the RSV G protein. The vaccine composition can also comprise an immunologically effective amount of all or a portion of RSV F protein. In particular embodiments, the vaccine compositions further comprise an adjuvant.

The invention further relates to a method of inhibiting induction of enhanced disease after vaccination and subsequent infection of a vertebrate with RSV, comprising administering an altered RSV G protein or polypeptide, where said altered G protein or polypeptide retains immunogenicity and, when incorporated into a vaccine and administered to a vertebrate, provides protection without inducing enhanced disease upon subsequent infection of the vertebrate with RSV.

The invention also relates to a vaccine comprising a physiologically acceptable vehicle and an effective amount of a nucleic acid molecule encoding an altered G protein or polypeptide of RSV, where said altered G protein or polypeptide retains immunogenicity and, when incorporated into a vaccine and administered to a vertebrate, provides protection without inducing enhanced disease upon subsequent infection of the vertebrate with RSV. In one embodiment, the vaccine further comprises a transfection-facilitating agent.

The invention also relates to a method of inducing an immune response in a vertebrate, comprising administering to said vertebrate an amount of DNA encoding an altered RSV G protein or polypeptide effective to induce an immune response, optionally with a transfection-facilitating agent, where said altered G protein or polypeptide retains immunogenicity and, when incorporated into a vaccine and administered to a vertebrate, provides protection without inducing enhanced disease upon subsequent infection of the vertebrate with RSV.

The invention also relates to a method of immunizing a vertebrate against RSV, comprising administering to the vertebrate a composition comprising an immunologically effective amount of altered G protein or polypeptide of RSV which retains immunogenicity and which, when incorporated into an immunogenic composition or vaccine and administered to a vertebrate, does not induce enhanced disease upon subsequent infection of the vertebrate with RSV.

The invention also pertains to a method of immunizing a vertebrate against RSV, comprising administering to the vertebrate a composition comprising an immunologically effective amount of a nucleic acid molecule encoding an altered G protein or polypeptide of RSV, where said altered G protein or polypeptide retains immunogenicity and, when incorporated into an immunogenic composition or vaccine and administered to a vertebrate, does not induce enhanced disease upon subsequent infection of the vertebrate with RSV.

In one embodiment, the composition further comprises an immunologically effective amount of all or a portion of RSV F protein, or a nucleic acid molecule encoding an immunologically effective amount of all or a portion of RSV F protein, respectively. In another embodiment, the vertebrate is an RSV seronegative human.

BRIEF DESCRIPTION OF THE DRAWINGS

FIG. 1A shows total leukocyte counts which were performed by trypan blue exclusion. FIG. 1B shows percent eosinophils in BAL which were determined by using the cell stain Diff-Quik. Data are presented as the mean count of 5 mice with error bars representing standard deviation.

FIG. 2 is a table of synthetic peptides (SEQ ID NOS: 1–31) corresponding to overlapping regions of the G protein of RSV. A series of overlapping peptides were synthesized by Genosys Biotechnologies, Inc. (The Woodlands, Tex.). The peptides spanned the region from amino acid 48 (which corresponds to the second translational start codon of G protein) to amino acid 294 of RSV A2 G protein. The purity of the peptides was determined by mass spectrometry. Lyophilized peptides were solubilized in sterile water to a concentration of 2 mg/ml and stored at −20° C.

FIG. 8 is a table showing that CD4 T cells mediate the eosinophilic response induced by RSV G protein and peptide 19-KLH. BALB/c mice (5 per group) were vaccinated intramuscularly at 0 and 4 weeks with either 1 μg of purified natural RSV G protein in 20 μg Stimulon™ QS-21; 250 μg KLH containing 18 μg peptide 19 adjuvanted with Stimulon™ QS-21; or intranasally with 50 μl of live RSV containing $10^6$ pfu. In order to deplete T cell subsets, the indicated monoclonal antibodies (or rat Ig as a control) were administered intraperitoneally at 14 and 20 days post-final immunization, at doses of 750 μg and 250 μg per mouse, respectively. At day 21 post-final vaccination, mice were challenged with live RSV and pulmonary eosinophilia quantitated by analysis of BAL 7 days thereafter. FACS analysis was performed using anti-CD4 and anti-CD8 fluorescent antibodies. Data are presented as the mean percent of eosinophils in BAL (±standard deviation) and as the percent of CD4+ to CD8+ cells as a function of total splenic lymphocytes. Significant differences (**) are indicated compared to similarly vaccinated control mice that received rat Ig.

DETAILED DESCRIPTION OF THE INVENTION

Figure 1A:
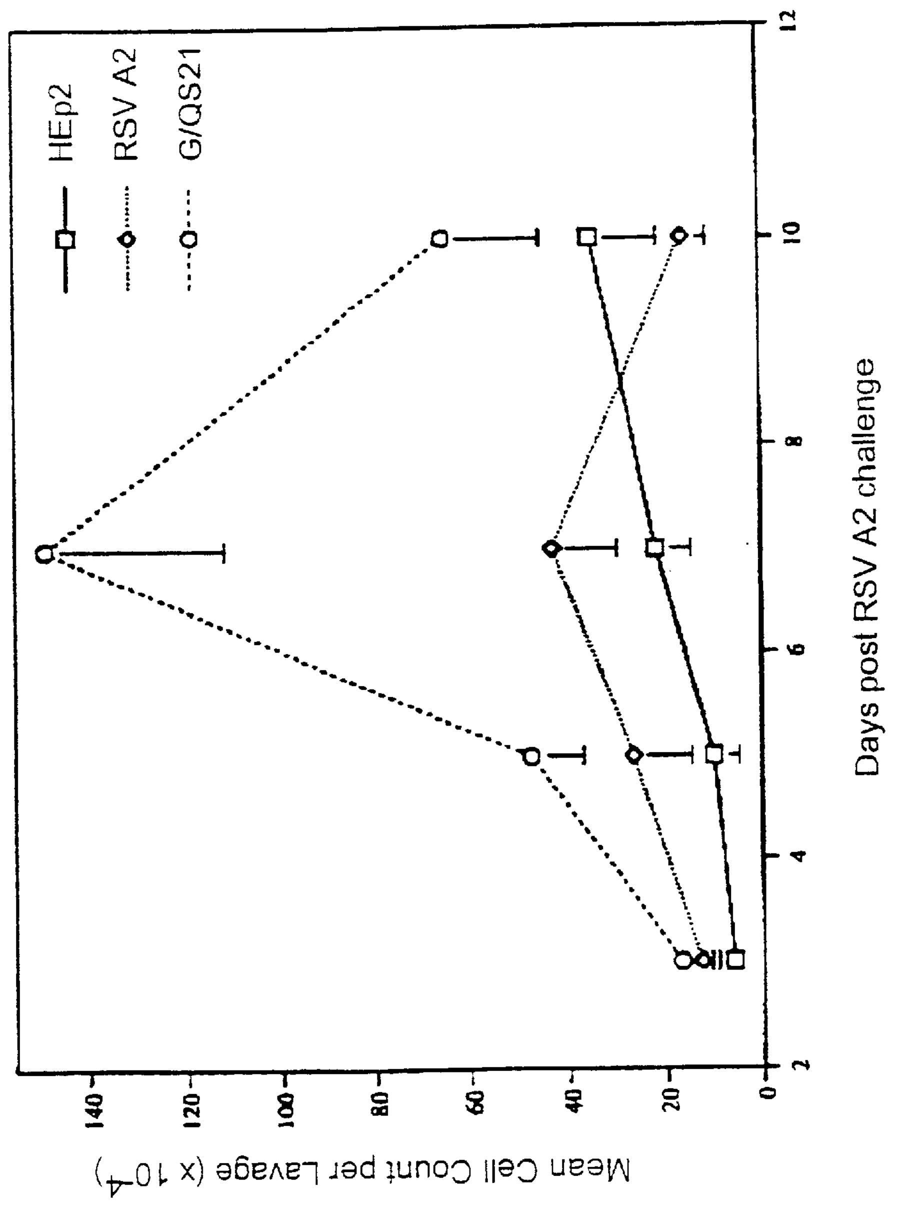
FIGS. 1A and 1B are graphs illustrating the kinetics of leukocyte stimulation in BAL. BALB/c mice were vaccinated with either 1 μg G protein adjuvanted with Stimulon™ QS-21 (20 μg/mouse), native RSV A2 (1–2×$10^6$ PFU), or mock HEp-2 cell lysate. Two weeks post secondary vaccination, mice were challenged with RSV and thereafter 5 representatives from each vaccination group were sacrificed at days 3, 5, 7 and 10, and BAL cells isolated.
Figure 1B:
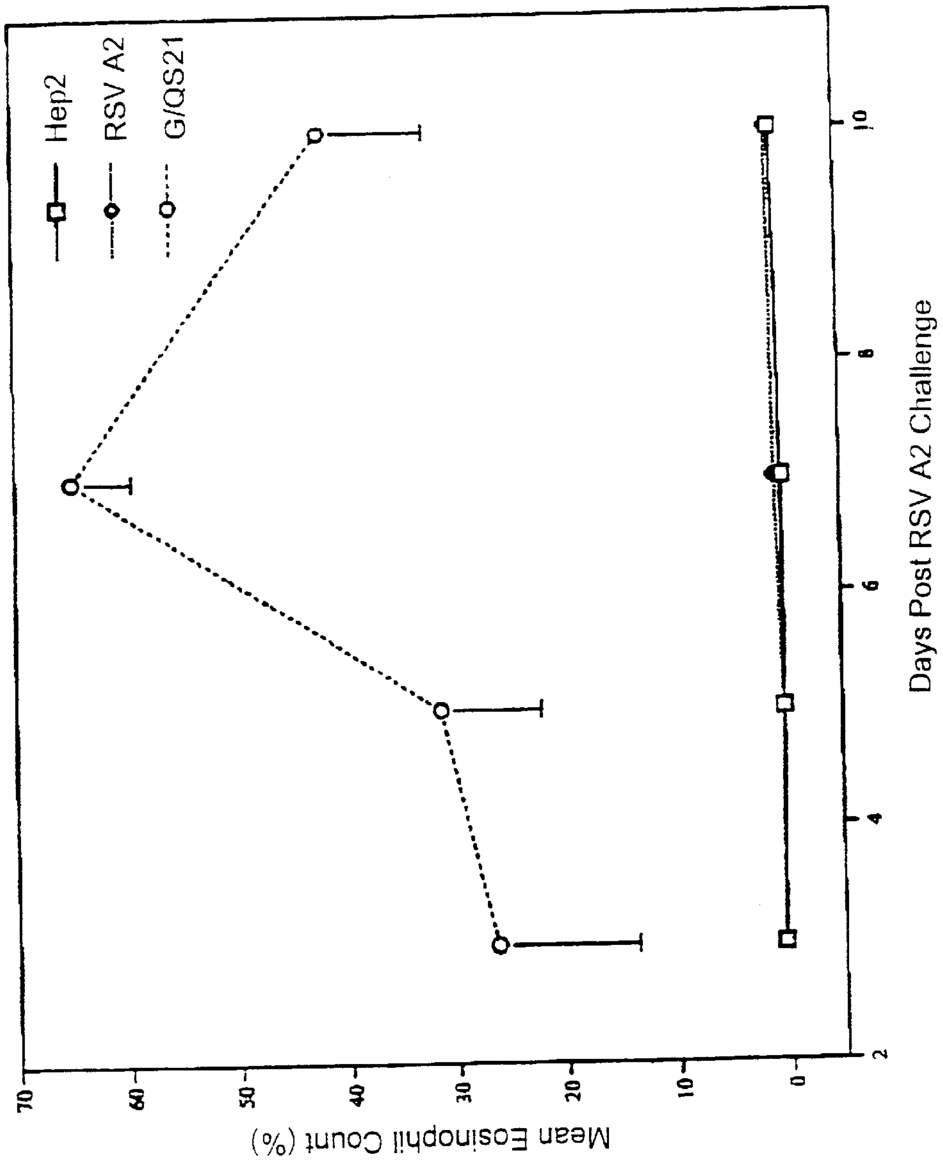

RSV G protein substantially augments the ability of F protein to protect BALB/c mice against challenge (Table). This suggests the inclusion of G protein in a subunit vaccine to RSV. However, the priming for pulmonary eosinophilia by G protein is both persistent and extensive, making it generally unsuitable for vaccine use. In quantitating the kinetics of influx of white blood cells into the BAL of vaccinated mice after challenge, it can be seen that the greatest cellular infiltrate ($1.42 \times 10^6$ cells) occurs at day 7 in mice vaccinated with G protein (FIG. 1A). Eosinophils were seen in response to vaccination with G protein throughout the 10-day time course, reaching a maximum of 65% of total white blood cells at day 7 (FIG. 1B).

The present invention relates to the synthesis of RSV G protein-derived proteins and/or polypeptides that do not result in the stimulation of pulmonary eosinophilia upon subsequent RSV infection. Specifically, the work described herein is directed to compositions and methods of preparation of proteins and/or polypeptides comprising altered G proteins or polypeptides that can be used as immunogens in vaccine formulations, including multivalent vaccines, and which can be used for active immunization. The strategy involves alteration of one or more amino acids in a specific region of the G protein sequence, resulting in a protein or polypeptide derived from RSV G protein that is immunogenic without priming for atypical pulmonary inflammation (e.g., pulmonary eosinophilia) or any form of enhanced RSV disease.

The wild type (native) nucleotide and amino acid sequences of the RSV G protein are known in the art (Wertz et al., *Proc. Natl. Acad. Sci. USA* 92:4075–4079 (1985); Satake et al., *Nucl. Acids Res.* 13(21): 7795–7810 (1985)). As used herein, "alteration" and its derivatives is intended to mean an amino acid sequence which is different from the wild type sequence, as well as a nucleotide sequence which encodes an amino acid sequence which is different from the wild type amino acid sequence. Alteration includes insertion, deletion and/or substitution of one or more nucleotides or amino acids.

For example, the alteration can be the insertion or deletion of a single nucleotide, or of more than one nucleotide, resulting in a frame shift mutation; the change of at least one nucleotide, resulting in a change in one or more encoded amino acids; the change of at least one nucleotide, resulting in the generation of a premature stop codon; the deletion of several nucleotides, resulting in a deletion of one or more amino acids encoded by the nucleotides; the insertion of one or several nucleotides, resulting in an interruption of the coding sequence of the gene; duplication of all or a part of the gene; transposition of all or a part of the gene; or rearrangement of all or a part of the gene. More than one such mutation may be present in a single gene. Such sequence changes cause an alteration in the G protein encoded by the gene. For example, if the alteration is a frame shift mutation, the frame shift can result in a change in the encoded amino acids, and/or can result in the generation of a premature stop codon, causing generation of a truncated protein.

For example, the alteration(s) can preferably preserve the three-dimensional configuration of the native G protein. Moreover, amino acids which are essential for the function of the G protein, particularly for immunogenicity, can be identified by methods known in the art. Particularly useful methods include identification of conserved amino acids, site-directed mutagenesis and alanine-scanning mutagenesis (for example, Cunningham and Wells, *Science* 244:1081–1085 (1989)), crystallization and nuclear magnetic resonance. The altered polypeptides produced by these methods can be tested for particular biologic activities, including immunogenicity, reduction in pulmonary eosinophilia and antigenicity.

Specifically, appropriate amino acid alterations can be made on the basis of several criteria, including hydrophobicity, basic or acidic character, charge, polarity, size, the presence or absence of a functional group (e.g., —SH or a glycosylation site), and aromatic character. Assignment of various amino acids to similar groups based on the properties above will be readily apparent to the skilled artisan; further appropriate amino acid changes can also be found in Bowie et al. (*Science* 247:1306–1310(1990)).

For example, with reference to the region of amino acid 184 to 198, the alteration can take the form of conservative (e.g., glycine for alanine; valine for isoleucine; asparagine for glutamine) site-directed mutation of the region 184 to 198 (amino acid sequence AICKRIPNKKPGKKT; SEQ ID NO: 19) which retains attributes of the region of the G protein involved in protective immune responses but deletes or modifies epitopes involved in the stimulation of pulmonary eosinophilia (i.e., a biological equivalent). The alteration can also take the form of non-conservative mutations (e.g., lysine for threonine; alanine for proline) wherein the deleterious stimulation of eosinophilia is reduced or abolished. The alteration can also take the form of complete deletion of the region 184–198 or any part thereof, with continued use of the remaining RSV G protein derived moiety. Deletions can be replaced by linker regions which retain the spatiality of the remaining G protein or polypeptide in order for optimal translation and/or immunogenicity. Alterations can be made using any standard mutagen or mutagenic process, such as site-directed mutation involving phages (e.g., M13) or use of polymerase chain reaction (PCR) technology involving synthetic oligonucleotides.

Accordingly, the invention pertains to a nucleotide sequence encoding an altered G protein of RSV, or portion thereof, wherein the altered G protein or portion thereof retains immunogenicity. As used herein, the term "altered G protein" is intended to mean a G protein (or portion thereof) of RSV which retains immunogenicity and which, when incorporated into an immunogenic composition or vaccine and administered to a vertebrate, does not induce enhanced disease (e.g., atypical pulmonary inflammation, such as pulmonary eosinophilia) upon subsequent infection with RSV. In a particular embodiment, the altered G protein comprises an alteration in the region from amino acid 184 to amino acid 198. In another embodiment, the alteration is in a region selected from the group consisting of the region from amino acid 159 to amino acid 198 of the RSV G protein, the region from amino acid 159 to amino acid 174 of the RSV G protein, the region from amino acid 171 to amino acid 187 of the RSV G protein, and the region from amino acid 176 to amino acid 190 of the RSV G protein.

Although the invention is specifically described with relation to the regions of RSV G protein comprising amino acids 184–198, 159–198, 159–174, 171–187 and 176–190, it is intended that the methodologies described herein used to identify these regions can be applied to additional regions of the wild type G protein to identify additional regions for alteration. For example, the regions upstream (toward the amino-terminus) and downstream (toward the carboxy-terminus) of the studied amino acid region (48 to 294) can be analyzed for additional domains in which alteration will produce beneficial effects. Alternatively, the region of amino acids from 48 to 294 can be re-analyzed with peptides having different overlaps to identify other domains in which alteration would be beneficial.

As appropriate, nucleic acid molecules of the present invention can be RNA, for example, mRNA, or DNA, such as cDNA and genomic DNA. DNA molecules can be double-stranded or single-stranded; single stranded RNA or DNA can be either the coding, or sense, strand or the non-coding, or antisense, strand. Preferably, the nucleic acid molecule comprises at least about 14 nucleotides, more preferably at least about 50 nucleotides, and even more preferably at least about 200 nucleotides. The nucleotide sequence can be only that which encodes at least a fragment of the amino acid sequence of the altered G protein; alternatively, the nucleotide sequence can include at least a fragment of the altered G protein amino acid coding sequence along with additional non-coding sequences such as introns and non-coding 3' and 5' sequences (including regulatory sequences, for example). Additionally, the nucleotide sequence can be fused to a marker sequence, for example, a sequence which encodes a polypeptide to assist in isolation or purification of the polypeptide. Such sequences include, but are not limited to, those which encode a glutathione-S-transferase (GST) fusion protein and those which encode a hemagglutinin A (HA) peptide marker from influenza.

The term "nucleotide sequence" can include a nucleotide sequence which is synthesized chemically or by recombinant means. Thus, recombinant DNA contained in a vector is included in the invention. Also, nucleotide sequences include recombinant DNA molecules in heterologous host cells, as well as partially or substantially purified DNA molecules in solution. In vivo and in vitro RNA transcripts of the DNA molecules of the present invention are also encompassed by nucleotide sequences of the invention. Such nucleotide sequences are useful, e.g., in the manufacture of the encoded altered G protein.

The invention also encompasses variations of the nucleotide sequences of the invention, such as those encoding portions, analogues or derivatives of the altered G protein, provided the portion, analogue or derivative comprises the altered G protein. Such variations can be naturally-occurring variations in the unaltered portion of the nucleotide sequence, such as in the case of allelic variation, or non-naturally-occurring, such as those induced by various mutagens and mutagenic processes. Intended variations include, but are not limited to, addition, deletion and substitution of one or more nucleotides which can result in conservative or non-conservative amino acid changes, including additions and deletions.

The invention described herein also relates to fragments of the nucleic acid molecules described above. The term "fragment" is intended to encompass a portion of a nucleotide sequence described herein which is from at least about 14 contiguous nucleotides to at least about 50 contiguous nucleotides or longer in length, providing that such fragments encode an altered G polypeptide; such fragments are useful as primers. Particularly preferred primers and probes selectively hybridize to the nucleic acid molecule encoding the altered G protein described herein. For example, fragments which encode antigenic portions of the altered G protein described herein are useful.

The invention also pertains to nucleotide sequences which hybridize under medium, and, more preferably, high stringency hybridization conditions (e.g., for selective hybridization) to a nucleotide sequence described herein. Appropriate stringency conditions are known to those skilled in the art or can be found in standard texts such as *Current Protocols in Molecular Biology*, John Wiley & Sons, N.Y. (1989), 6.3.1–6.3.6.

Accordingly, the invention pertains to nucleotide sequences which have a substantial identity with the altered nucleotide sequences described herein; particularly preferred are nucleotide sequences which have at least about 90%, and more preferably at least about 95% identity with nucleotide sequences described herein. Particularly preferred in this instance are nucleotide sequences encoding polypeptides having substantially similar immunogenic activity as the altered G protein described herein.

This invention also pertains to an altered G protein or polypeptide of RSV. The altered G protein or polypeptide is a G protein (or portion thereof) of RSV which retains immunogenicity and which, when incorporated into an immunogenic composition or vaccine and administered to a vertebrate, does not induce enhanced disease (e.g., atypical pulmonary inflammation such as pulmonary eosinophilia) upon subsequent infection with RSV. In a particular embodiment, the altered G protein comprises at least one alteration in the region from amino acid 184 to amino acid 198. In another embodiment, the alteration is in a region selected from the group consisting of the region from amino acid 159 to amino acid 198 of the RSV G protein, the region from amino acid 159 to amino acid 174 of the RSV G protein, the region from amino acid 171 to amino acid 187 of the RSV G protein, and the region from amino acid 176 to amino acid 190 of the RSV G protein. The altered G protein of the invention can be partially or substantially purified (e.g., purified to homogeneity), and/or is substantially free of other proteins.

The altered G protein or polypeptide can also be a fusion protein comprising all or a portion of the altered G protein amino acid sequence fused to an additional component. Additional components, such as radioisotopes and antigenic tags, can be selected to assist in the isolation or purification of the polypeptide or to extend the half life of the polypeptide; for example, a hexahistidine tag would permit ready purification by nickel chromatography. Alternatively, the altered G protein or polypeptide can be a fusion protein comprising all or a portion of the altered G protein amino acid sequence fused to all or a portion of the RSV F protein amino acid sequence (Collins et al., *Proc. Natl. Acad. Sci* (*USA*) 81:7683–7687 (1984); U.S. Pat. No. 5,639,853; U.S. Pat. No. 5,723,130).

The invention also includes altered G proteins and polypeptides which comprise additional amino acid alterations beyond those alterations necessary to prevent production of enhanced disease in a vertebrate to which the altered protein or polypeptide is administered. For example, amino acid alterations, e.g., conservative amino acid changes which do not impact on the disease characteristics resulting from administration of the altered protein are included in the invention. Also included in the invention are polypeptides which are at least about 40% identical to the altered G protein or polypeptide described herein. However, polypeptides exhibiting lower levels of identity are also useful, particular if they exhibit high, e.g., at least about 40%, identity over one or more particular domains of the protein. For example, altered polypeptides sharing high degrees of identity over domains necessary for particular activities, including immunogenic function and receptor binding activity, are included herein. Polypeptides described herein can be chemically synthesized or recombinantly produced.

To determine the percent identity of two polypeptide sequences, the sequences are aligned for optimal comparison purposes (e.g., gaps can be introduced in the sequence of a first amino acid sequence). The amino acid residues at corresponding amino acid positions are then compared. When a position in the first sequence is occupied by the same amino acid residue as the corresponding position in the second sequence, then the molecules are identical at that position. The percent identity between the two sequences is a function of the number of identical positions shared by the sequences (i.e., % identity=# of identical positions/total # of positions×100).

The determination of percent identity between two sequences can be accomplished using a mathematical algorithm. A preferred, non-limiting example of a mathematical algorithm utilized for the comparison of two sequences is the algorithm of Karlin et al., *Proc. Natl. Acad. Sci. USA*, 90:5873–5877 (1993). Such an algorithm is incorporated into the NBLAST and XBLAST program, score=50, wordlength=3, to obtain amino acid sequences having the desired identity to polypeptide or protein molecules of the invention. To obtain gapped alignments for comparison purposes, Gapped BLAST can be utilized as described in Altschul et al., *Nucleic Acids Res*, 25:3389–3402 (1997). When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers et al., CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent of identity between two sequences can be determined using techniques similar to those described above, with or without allowing gaps. In calculating percent identity, only exact matches are counted.

The invention also provides expression vectors, e.g., nucleic acid constructs, containing a nucleic acid sequence encoding an altered G protein or polypeptide, operably linked to at least one regulatory sequence. Many such vectors are commercially available, and other suitable vectors can be readily prepared by the skilled artisan. "Operably linked" is intended to mean that the nucleotide sequence is linked to a regulatory sequence in a manner which allows expression of the nucleic acid sequence; this term is intended to include both direct physical linkage and linkage by means of a linker or intervening sequence. Regulatory sequences are art-recognized and are selected to produce a polypeptide which is an altered G protein or polypeptide. Accordingly, the term "regulatory sequence" includes promoters, enhancers, and other expression control elements which are described in Goeddel, *Gene Expression Technology: Methods in Enzymology* 185, Academic Press, San Diego, Calif. (1990). For example, the native regulatory sequences or regulatory sequences native to the transformed host cell can be employed. It should be understood that the design of the expression vector may depend on such factors as the choice of the host cell to be transformed and/or the type of protein desired to be expressed.

For instance, the altered G proteins and polypeptides of the present invention can be produced by ligating the nucleic acid molecule, or a portion thereof, into a vector suitable for expression in either prokaryotic cells, eukaryotic cells or both (see, for example, Broach, et al., *Experimental Manipulation of Gene Expression*, ed. M. Inouye (Academic Press, 1983) p.83; *Molecular Cloning: A Laboratory Manual*, 2nd Ed., ed. Sambrook et al. (Cold Spring Harbor Laboratory Press, 1989) Chapters 16 and 17). Typically, expression constructs will contain one or more selectable markers, including, but not limited to, the gene that encodes dihydrofolate reductase and the genes that confer resistance to neomycin, tetracycline, ampicillin, chloramphenicol, kanamycin and streptomycin resistance.

The expression construct can comprise a regulatory sequence operably linked to a nucleic acid molecule encoding an altered G protein or polypeptide, optionally linked, either directly or by means of a polynucleotide linker, to a nucleic acid molecule encoding all or a portion of the RSV F protein. Expression of such an expression construct will result in a chimera comprising an altered G protein or polypeptide and all or a portion of an F protein or polypeptide; if a polynucleotide linker is utilized in the construct, the F and altered G polypeptides will be linked by one or more amino acids. Methods for preparing and expressing F/G chimeras in general are taught, e.g., in U.S. Pat. No. 5,194,595 (Wathen), the teachings of which are incorporated herein by reference.

Prokaryotic and eukaryotic host cells transfected by the described vectors are also provided by this invention. For instance, cells which can be transfected with the vectors of the present invention include, but are not limited to, bacterial cells such as *E. coli* (e.g., *E. coli* K12 strains), Streptomyces, Pseudomonas, *Serratia marcescens* and *Salmonella typhimurium*, insect cells (baculovirus), including Drosophila, fungal cells, such as yeast cells, plant cells and mammalian cells, such as thymocytes, Chinese hamster ovary (CHO) cells, HEp-2 cells, Vero cells and COS cells.

Thus, a nucleotide sequence encoding the altered G protein or polypeptide described herein can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect, plant or mammalian) or prokaryotic (bacterial cells), are standard procedures used in producing other well known proteins. Viral vectors include, but are not limited to, adenoviruses and Venezuelan equine encephalitis vector. In addition, Vaccinia virus (VV) has been used to express in mammalian cell lines, or deliver to animal models, various proteins of RSV (Olmstead et al., *PNAS* 83:7462–7466 (1986); Wertz et al., *J. Virol* 63:4767–4776 (1989)). Likewise, similar constructs with the altered cDNA for RSV G protein inserted into the thymidine kinase gene of VV may be utilized to synthesize the altered G protein or polypeptide. For example, the methods detailed by Ball et al., (*Proc. Natl. Acad. Sci. USA* 83:246–250 (1986)) or Olmstead et al., (*Proc. Natl. Acad. Sci. USA* 83:7462–7466 (1986)) can be used to express the altered G protein or the F protein/altered G protein chimera from vaccinia virus vectors. Similar procedures, or modifications thereof, can be employed to prepare recombinant proteins according to the present invention by microbial means or tissue-culture technology. Accordingly, the invention pertains to the production of altered G proteins or polypeptides by recombinant technology.

In addition to the foregoing host cell systems in which the altered G proteins or polypeptides of this invention are produced in vitro, a variety of systems are appropriate for expression and delivery of such altered G proteins and polypeptides in vivo. These systems utilize attenuated pathogens such as bacteria or viruses as delivery agents. These live attenuated pathogens have inserted within them as a heterologous nucleic acid segment the nucleic acid sequence encoding the desired altered G proteins or polypeptides of this invention. Using these systems, the desired altered G proteins or polypeptides are expressed by a live, attenuated bacterium or virus within the body of a vertebrate.

Examples of such live attenuated pathogens include, but are not limited to, the live attenuated bacteria such as Salmonella which are described in U.S. Pat. No. 4,837,151, which is particularly suitable for oral delivery, and the live attenuated Venezuelan Equine Encephalitis virus described in U.S. Pat. No. 5,643,576, which is particularly suitable for intranasal or inhalation delivery.

The proteins and polypeptides of the present invention can be isolated or purified (e.g., to homogeneity) from recombinant cell culture by a variety of processes. These include, but are not limited to, anion or cation exchange chromatography, ethanol precipitation, affinity chromatography and high performance liquid chromatography (HPLC). The particular method used will depend upon the properties of the polypeptide and the selection of the host cell; appropriate methods will be readily apparent to those skilled in the art.

The present invention also relates to antibodies which bind an altered G protein or polypeptide. For instance, polyclonal and monoclonal antibodies, including non-human and human antibodies, humanized antibodies, chimeric antibodies and antigen-binding fragments thereof (*Current Protocols in Immunology*, John Wiley & Sons, N.Y. (1994); EP Application 173,494 (Morrison); International Patent Application WO86/01533 (Neuberger); and U.S. Pat. No. 5,225,539 (Winters)) which bind to the described altered G protein are within the scope of the invention. A mammal, such as a mouse, rat, hamster or rabbit, can be immunized with an immunogenic form of the altered G protein or polypeptide. Techniques for conferring immunogenicity on a protein or peptide include conjugation to carriers or other techniques well known in the art. The protein or polypeptide can be administered in the presence of an adjuvant. The progress of immunization can be monitored by detection of antibody titers in plasma or serum. Standard ELISA or other immunoassays can be used with the immunogen as antigen to assess the levels of antibody.

Following immunization, anti-peptide antisera can be obtained, and if desired, polyclonal antibodies can be isolated from the serum. Monoclonal antibodies can also be produced by standard techniques which are well known in the art (Kohler and Milstein, *Nature* 256:495–497 (1975); Kozbar et al., *Immunology Today* 4:72 (1983); and Cole et al., *Monoclonal Antibodies and Cancer Therapy*, Alan R. Liss, Inc., pp. 77–96 (1985)). The term "antibody" as used herein is intended to include fragments thereof, such as Fab and $F(ab)_2$. Antibodies described herein can be used to inhibit the activity of the altered G protein described herein, particularly in vitro and in cell extracts, using methods known in the art. As used herein, "inhibition" is intended to mean any reduction in quantity or quality, including complete absence. Additionally, such antibodies, in conjunction with a label, such as a radioactive label, can be used to assay for the presence of the expressed protein in a cell from, e.g., a tissue sample or cell culture, and can be used in an immunoabsorption process, such as an ELISA, to isolate the altered G protein or polypeptide. Tissue samples which can be assayed include human tissues, e.g., differentiated and non-differentiated cells. Examples include lung, bone marrow, thymus, kidney, liver, brain, pancreas, fibroblasts and epithelium.

The present invention also pertains to pharmaceutical compositions comprising altered G proteins and polypeptides described herein. For instance, an altered G polypeptide or protein, or prodrug thereof, of the present invention can be formulated with a physiologically acceptable medium to prepare a pharmaceutical composition (e.g., an immunogenic composition). The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to well known procedures, and will depend on the ultimate pharmaceutical formulation desired. Methods of introduction of exogenous peptides at the site of treatment include, but are not limited to, intradermal, intramuscular, intraperitoneal, intravenous, subcutaneous, oral and intranasal. Other suitable methods of introduction can also include gene therapy, rechargeable or biodegradable devices, aerosols and slow release polymeric devices. The altered G protein can be administered in conjunction with additional immunogens, including all or a portion of RSV F protein; the altered G protein or polypeptide can be administered separately, sequentially or concurrently with the additional immunogen. For example, the altered G protein or polypeptide can be given in an admixture with all or a portion of RSV F protein.

The altered G protein or polypeptide (or admixture, fusion protein or chimera thereof) can be used as antigen to elicit an immune response to the antigen in a vertebrate, such as a mammalian host. For example, the antigen can be all or an immunogenic portion of the altered G protein or a chimera of the altered G protein or polypeptide and all or an immunogenic portion of the RSV F protein. The descriptions herein relating to compositions comprising an altered G protein or polypeptide are intended to include compositions comprising an altered G protein or polypeptide along with all or a portion of the RSV F protein.

The method of the present invention comprises administering to the vertebrate an immunologically effective dose of a vaccine composition comprising a mixture of an altered G protein or polypeptide and any suitable adjuvant. As used herein, an "adjuvant" is intended to mean any agent which is sufficient to enhance or modify the immune response to the vaccine antigen. As used herein, an "immunologically effective" dose of the vaccine composition is a dose which is suitable to elicit an immune response. The particular dosage will depend upon the age, weight and medical condition of the vertebrate to be treated, as well as on the method of administration. Suitable doses will be readily determined by the skilled artisan. The vaccine composition can be optionally administered in a pharmaceutically or physiologically acceptable vehicle, such as physiological saline or ethanol polyols such as glycerol or propylene glycol.

Suitable adjuvants include vegetable oils or emulsions thereof, surface active substances, e.g., hexadecylamin, octadecyl amino acid esters, octadecylamine, lysolecithin, dimethyl-dioctadecylammonium bromide, N,N-dicoctadecyl-N'-N'bis (2-hydroxyethyl-propane diamine), methoxyhexadecylglycerol, and pluronic polyols; polyamines,e.g., pyran, dextransulfate, poly IC, carbopol; peptides, e.g., muramyl dipeptide, dimethylglycine, tuftsin; immune stimulating complexes; oil emulsions; mineral gels; aluminum compounds such as aluminum hydroxide and aluminum phosphate; MPLTM (3-O-deacylated monophosphoryl lipid A, RIBI ImmunoChem Research, Inc., Hamilton, Mont.); detoxified mutants of Cholera toxin and *E. coli* heat labile toxin; naked DNA CpG motifs; and Stimulon™ QS-21 (Aquila Biopharmaceuticals, Inc., Framingham, Mass.). The altered G protein or polypeptide of this invention can also be incorporated into liposomes or ISCOMS (immunostimulating complexes), and supplementary active ingredients may also be employed. The antigens of the present invention can also be administered in combination with lymphokines, including, but not limited to, IL-2, IL-3, IL-12, IL-15, IFN-γ and GM-CSF.

The compositions and vaccines of this invention can be administered to a human or animal by a variety of routes, including parenteral, intrarterial, intradermal, transdermal (such as by the use of slow release polymers), intramuscular, intraperitoneal, intravenous, subcutaneous, oral and intranasal routes of administration. The amount of altered G protein employed in such vaccines will vary depending upon the route of administration and physical characteristics of the subject vertebrate. Adjustment and manipulation of established dosage ranges used with traditional carrier antigens for adaptation to the present vaccine is well within the ability of those skilled in the art. The vaccines of the present invention are intended for use in the treatment of both immature and adult vertebrates, and, in particular, humans.

The altered G protein or polypeptide of the present invention can be coupled to a carrier molecule in order to modulate or enhance the immune response. Suitable carrier proteins include bacterial toxins which are safe for administration to vertebrates and immunologically effective as carriers. Examples include pertussis, diphtheria, and tetanus toxoids and non-toxic mutant proteins (cross-reacting materials (CRM)), such as the non-toxic variant of diphtheria toxoid, $CRM_{197}$. Fragments of the native toxins or toxoids, which contain at least one T-cell epitope, are also useful as carriers for antigens. Methods for preparing conjugates of antigens and carrier molecules are well known in the art and can be found, for example, in Wong, *Chemistry of Protein Conjugation* (CRC Press Inc., Ann Arbor, Mich. (1991)); Bernatowicz and Matsueda, *Analytical Biochemistry* 155:95–102 (1986); Frisch et al., *Bioconjugate Chem.* 7:180–186 (1996); and Boeckler et al., *J. Immunological Methods* 191:1–10 (1996).

In addition, if a particular peptide region (e.g., amino acids 184–198, amino acids 159–174, amino acids 171–187, amino acids 176–190) is deleted, one or more epitopes from an antigen from another organism, including, but not limited to, parainfluenza virus type 3, can be inserted into the deleted region, in order to create a bivalent vaccine.

The invention also relates to a vaccine comprising a nucleic acid molecule encoding an altered G protein or polypeptide of RSV, wherein said altered G protein or polypeptide retains immunogenicity and, when incorporated into an immunogenic composition or vaccine and administered to a vertebrate, provides protection without inducing enhanced disease upon subsequent infection of the vertebrate with RSV, and a physiologically acceptable vehicle. Such a vaccine is referred to herein as a nucleic acid vaccine or DNA vaccine and is useful for the genetic immunization of vertebrates.

The term, "genetic immunization", as used herein, refers to inoculation of a vertebrate, particularly a mammal, with a nucleic acid vaccine directed against a pathogenic agent, particularly RSV, resulting in protection of the vertebrate against RSV. A "nucleic acid vaccine" or "DNA vaccine" as used herein, is a nucleic acid construct comprising a nucleic acid molecule encoding a polypeptide antigen, particularly an altered G protein or polypeptide of RSV described herein. The nucleic acid construct can also include transcriptional promoter elements, enhancer elements, splicing signals, termination and polyadenylation signals, and other nucleic acid sequences. "Protection against RSV" as used herein refers to generation of an immune response in the vertebrate, the immune response being protective (partially or totally) against manifestations of the disease caused by RSV. A vertebrate that is protected against disease caused by the RSV virus may be infected with RSV, but to a lesser degree than would occur without immunization; may be infected with RSV, but does not exhibit disease symptoms; or may be infected with RSV, but exhibits fewer disease symptoms than would occur without immunization. Alternatively, the vertebrate that is protected against disease caused by RSV may not become infected with the RSV virus at all, despite exposure to the virus. In all cases, however, the nucleic acid vaccine does not induce enhanced disease upon subsequent infection of the vertebrate with RSV.

The nucleic acid vaccine can be produced by standard methods. For example, using known methods, a nucleic acid (e.g., DNA) encoding an altered G protein or polypeptide of RSV, can be inserted into an expression vector to construct a nucleic acid vaccine (see Maniatis et al., *Molecular Cloning, A Laboratory Manual*, 2nd edition, Cold Spring Harbor Laboratory Press (1989)).

The individual vertebrate is inoculated with the nucleic acid vaccine (i.e., the nucleic acid vaccine is administered), using standard methods. The vertebrate can be inoculated subcutaneously, intravenously, intraperitoneally, intradermally, intramuscularly, topically, orally, rectally, nasally, buccally, vaginally, by inhalation spray, or via an implanted reservoir in dosage formulations containing conventional non-toxic, physiologically acceptable carriers or vehicles. Alternatively, the vertebrate is inoculated with the nucleic acid vaccine through the use of a particle acceleration instrument (a "gene gun"). The form in which it is administered (e.g., capsule, tablet, solution, emulsion) will depend in part on the route by which it is administered. For example, for mucosal administration, nose drops, inhalants or suppositories can be used.

The nucleic acid vaccine can be administered in conjunction with any suitable adjuvant. The adjuvant is administered in a sufficient amount, which is that amount that is sufficient to generate an enhanced immune response to the nucleic acid vaccine. The adjuvant can be administered prior to (e.g., 1 or more days before) inoculation with the nucleic acid vaccine; concurrently with (e.g., within 24 hours of) inoculation with the nucleic acid vaccine; contemporaneously (simultaneously) with the nucleic acid vaccine (e.g., the adjuvant is mixed with the nucleic acid vaccine, and the mixture is administered to the vertebrate); or after (e.g., 1 or more days after) inoculation with the nucleic acid vaccine. The adjuvant can also be administered at more than one time (e.g., prior to inoculation with the nucleic acid vaccine and also after inoculation with the nucleic acid vaccine). As used herein, the term "in conjunction with" encompasses any time period, including those specifically described herein and combinations of the time periods specifically described herein, during which the adjuvant can be administered so as to generate an enhanced immune response to the nucleic acid vaccine (e.g., an increased antibody titer to the antigen encoded by the nucleic acid vaccine, or an increased antibody titer to RSV). The adjuvant and the nucleic acid vaccine can be administered at approximately the same location on the vertebrate; for example, both the adjuvant and the nucleic acid vaccine are administered at a marked site on a limb of the vertebrate.

In a particular embodiment, the nucleic acid construct is co-administered with a transfection-facilitating agent. In a preferred embodiment, the transfection-facilitating agent is dioctylglycylspermine (DOGS) (published PCT application publication no. WO96/21356). In another embodiment, the transfection-facilitating agent is bupivicaine (U.S. Pat. No. 5,593,972).

The invention also provides a method of inducing an immune response in a vertebrate, comprising administering to the vertebrate an immunogenic composition, vaccine or nucleic acid vaccine described herein in an amount effective to induce an immune response. In a particular embodiment, the immune response comprises reduced IL-5 secretion and/or increased IFN-γ secretion relative to an immune response induced by a native RSV G protein. In another embodiment, the immune response is preferably oriented toward a type 1 response instead of a type 2 response. In a particular embodiment, the vertebrate is a seronegative vertebrate, e.g., a seronegative human. The invention also provides a method of immunizing a vertebrate, e.g., an RSV seronegative human, against RSV, comprising administering to the vertebrate a composition comprising an immunologically effective amount of altered G protein or polypeptide of RSV which retains immunogenicity and which, when incorporated into an immunogenic composition or vaccine and administered to a vertebrate, does not induce enhanced disease upon subsequent infection of the vertebrate with RSV. Alternatively, the composition comprises a nucleic acid molecule encoding an immunologically effective amount of altered G protein or polypeptide of RSV which retains immunogenicity and which, when incorporated into an immunogenic composition or vaccine and administered to a vertebrate, does not induce enhanced disease upon subsequent infection of the vertebrate with RSV. The invention also relates to a method of vaccinating a vertebrate, comprising administering to the vertebrate a vaccine or nucleic acid vaccine described herein.

Figures 10A, 10B, 10C:
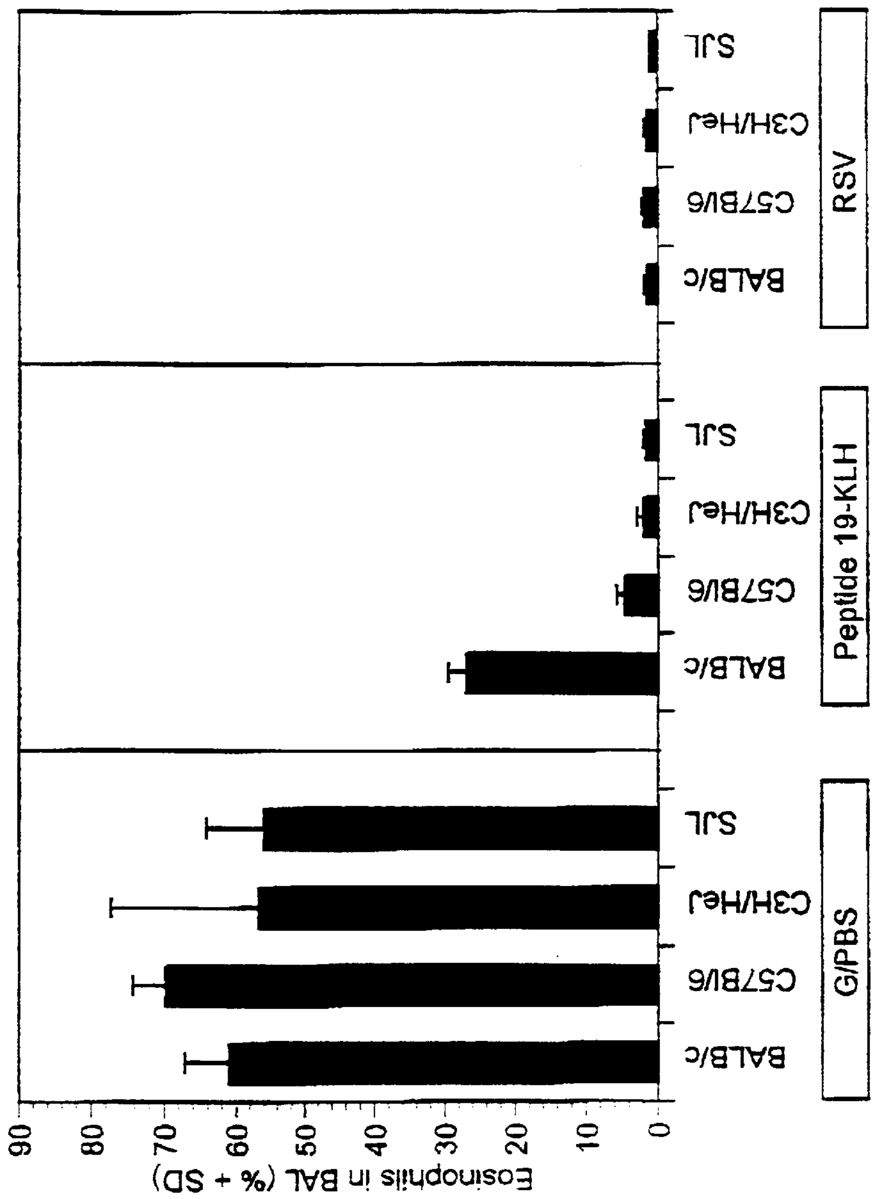
FIGS. 10A–10C are graphs showing the priming of multiple mouse strains for pulmonary eosinophilia with G protein and peptide 19. BALB/c mice, C57BI/6, SJL and C3H/HeJ mice (5 mice per group) were vaccinated intramuscularly at 0 and 4 weeks. The vaccines consisted of 1 $\mu$g G protein in PBS (G/PBS); 250 $\mu$g KLH containing 13 $\mu$g peptide 19 adjuvanted with 20 $\mu$g of QS-21 per mouse (peptide 19-KLH); or live RSV ($10^6$ pfu/mouse) (RSV). Two weeks post-secondary vaccination, mice were challenged with live RSV (approximately $10^6$ pfu/mouse). Data are presented as the mean percent (±standard deviation) of eosinophils in BAL fluids 7 days after challenge.
Figure 11A:
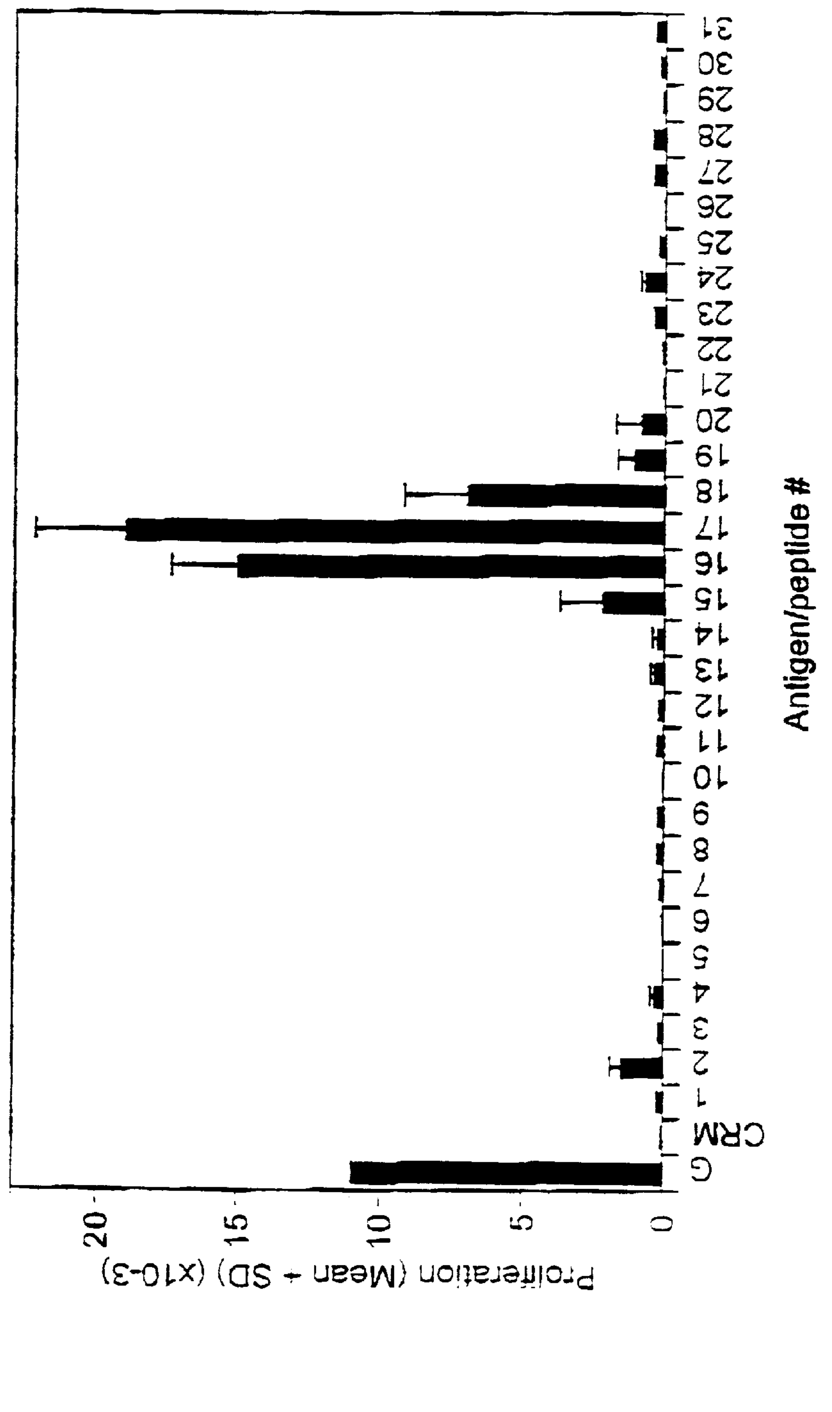
FIGS. 11A–11C are graphs showing the proliferative responses of G protein-primed splenocytes from multiple strains of mice after stimulation with peptides of G protein. C57BI/6 mice (FIG. 11A), SJL mice (FIG. 11B) and C3H/HeJ mice (FIG. 11C) were vaccinated at 0 and 4 weeks with 1 $\mu$g G protein in PBS. Two weeks post-secondary vaccination, splenocytes from 5 mice were isolated, pooled and cultured in the presence of antigen for 3 days. Each synthetic peptide (1–31) was supplied at a concentration of 50 $\mu$g/ml. Natural G protein was added at a concentration of 0.5 $\mu$g/ml. As a control, cultures were also stimulated with $CRM_{197}$ (CRM). Data are presented as the mean (±standard deviation) of triplicate wells.
Figure 11B:
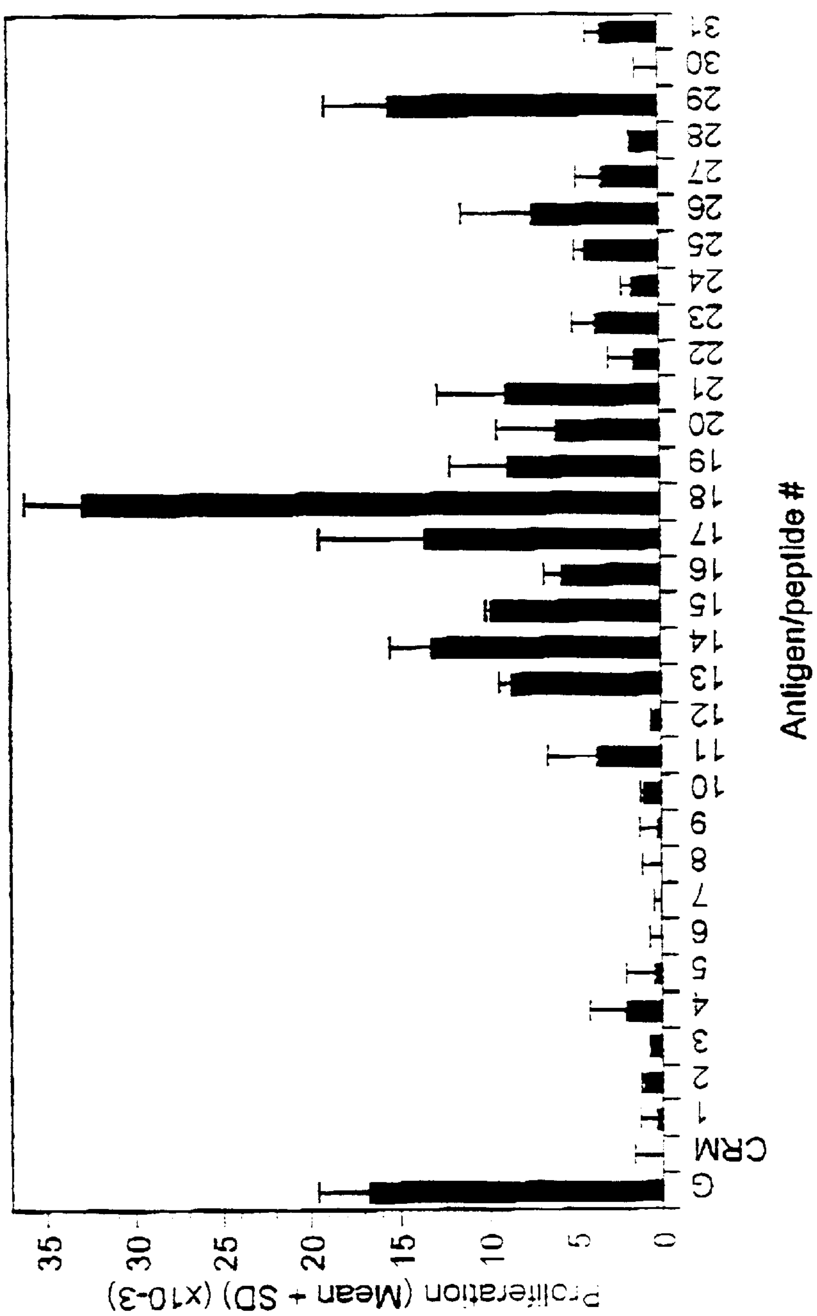
Figure 11C:
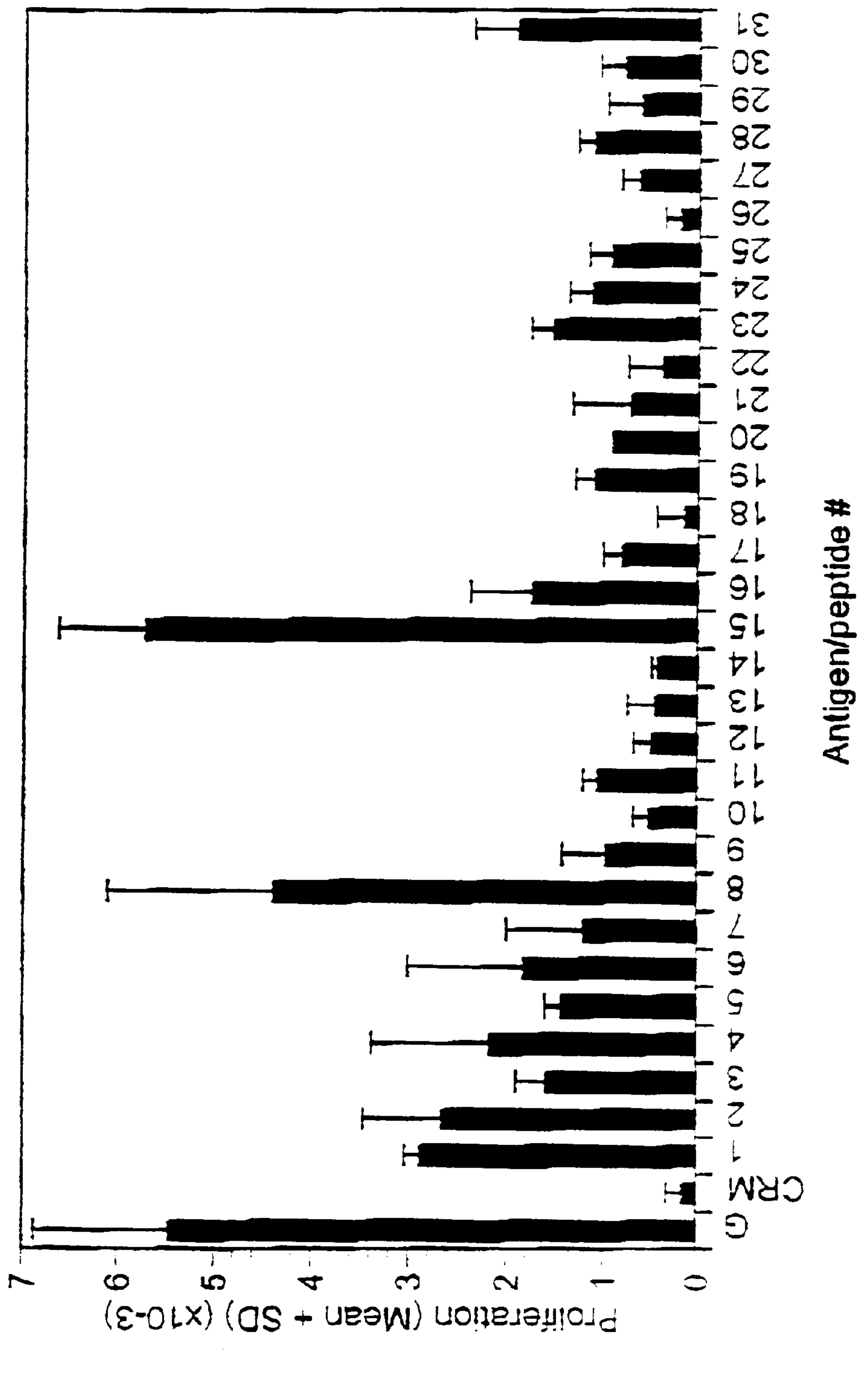

Collectively, the data described herein show that peptide 19 (AICKRIPNKKPGKKT) (SEQ ID NO: 19) primes for pulmonary eosinophilia by stimulating the expansion of $CD4^+$ T cells destined to secrete IL-5, a cytokine associated with the induction and recruitment of eosinophils, upon restimulation (Coffman et al., *Science* 245:308–310 (1989)). Whereas vaccination with peptide 184–198 was associated with significant eosinophilia in BALB/c mice (27%), comparatively less eosinophilia was observed in C57BL/6 (5%), C3H/HeJ (2%) or SJL (2%) mice (FIG. 10B). In accordance with a MHC influence upon immune responsiveness to peptide 184–198, in vitro stimulation assays of primed spleen cells showed a varied proliferative response to overlapping peptides of G protein (FIGS. 11A–11C). Splenocytes from C57BL/6, SJL and C3H/HeJ mice responded maximally to peptides encompassing amino acids 171–187, 176–190 and 159–174, respectively (FIGS. 11A, 11B and 11C, respectively).

Figure 6:
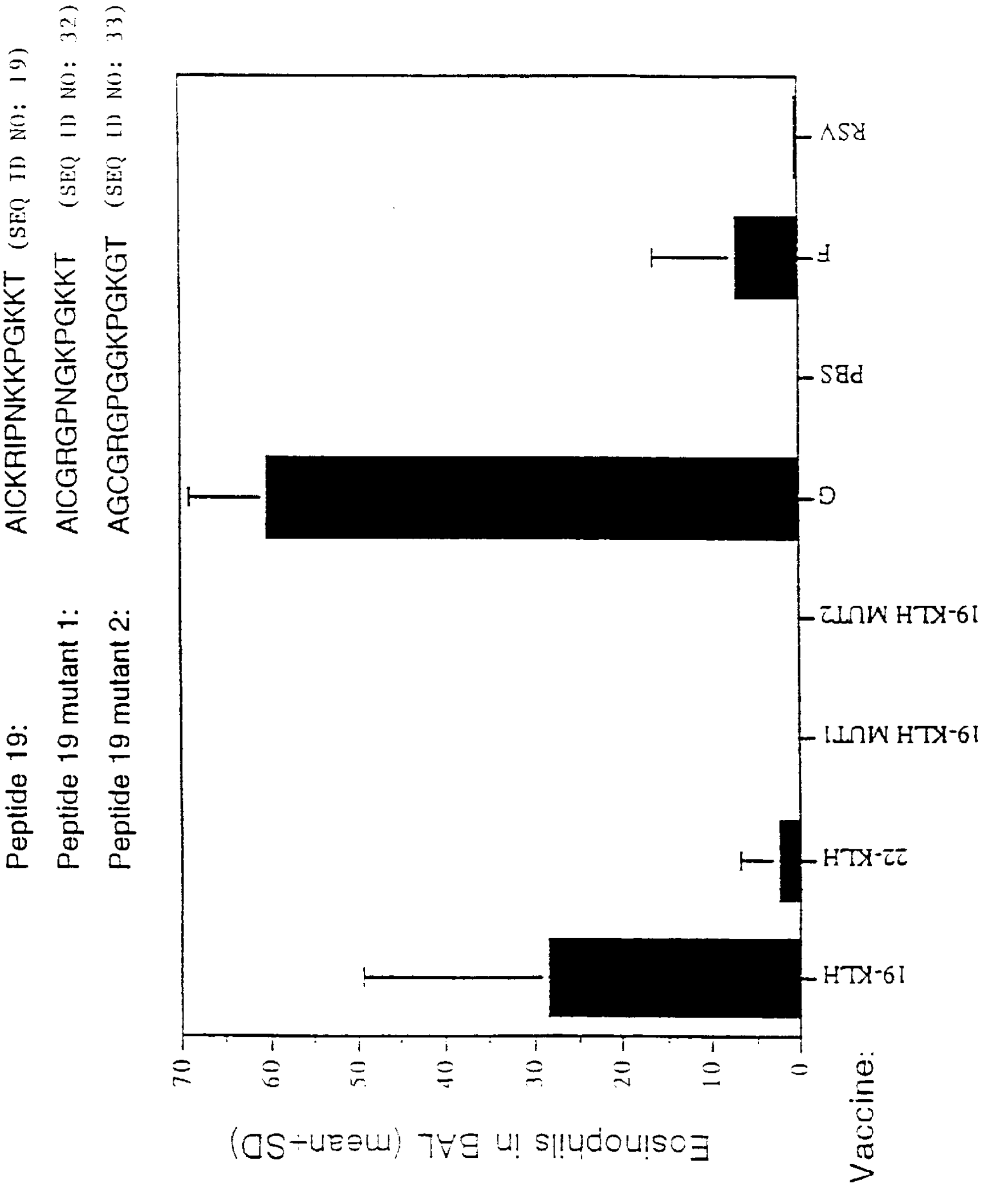
FIG. 6 is a bar graph showing the identification of a T cell epitope in peptide 19 that facilitates the eosinophilic response. BALB/c mice (5 per group) were vaccinated intramuscularly at 0 and 4 weeks with either 1 μg of native purified RSV G protein in 20 μg Stimulon™ QS-21; 250 μg peptide 19-KLH; 250 μg peptide 22-KLH; 250 μg mutant peptide 19-1-KLH or 250 μg mutant peptide 19-2-KLH or intranasally with a 50 μl volume of live RSV containing $10^6$ pfu. Two weeks post-secondary vaccination, mice were challenged with live RSV and pulmonary eosinophilia quantitated by analysis of BAL 7 days thereafter. Data are presented as the mean percent of eosinophils in BAL (±standard deviation).

Without wishing to be bound by theory, a model of immune priming is suggested in which one or more Th cell epitopes within the described regions control the qualitative nature of subsequent immune responses, resulting in a profound skewing toward the Th2 phenotype. That the peptide component of the T cell receptor (TCR)-MHC interaction can modulate the quality of the immune response between Th1 and Th2 phenotypes has previously been shown by altering peptide sequences (Pfieffer et al., *J. Exp. Med.* 181:1569–1574 (1995); Murray et al., *Eur. J. Immunol.* 24:2337–2344 (1994)). However, it remains possible that the 15 amino acids that comprise peptide 19 contain more than one T cell epitope, each with a discrete ability to stimulate a Th1 versus Th2 response. In favor of this hypothesis, an analysis of the sequence of peptide 19 indicates that it contains three potential T cell epitopes restricted to MHC class II I-$E^d$ which align closely at the critical 1, 4, 6 and 9 anchor residues (I, K or R, I, and K, respectively) (amino acids 187, 189 and 192 of peptide 19)(Rammensee et al., *Immunogenetics* 41:178–228 (1995)). Each of these putative sequences is consistent with class II binding based upon the publication of known ligands generated by the biochemical isolation of MHC-associated peptides or by peptide binding assays (Rammensee et al., *Immunogenetics* 41:178–228 (1995)). The mutation of peptide 19 (AICKRIPNKKPGKKT) (SEQ ID NO. 19) to a sequence which disrupts the critical MHC-binding anchor regions of the potential T cell epitopes (AICGRGPNGKPGKKT (mutant 1; SEQ ID NO. 32) or AGCGRGPGGKPGKGT (mutant 2; SEQ ID NO: 33)) completely abrogated the ability of this peptide to predispose mice for pulmonary eosinophilia (FIG. 6). Moreover, the data presented in FIG. 9 suggest that a more selective mutational analysis can result in sequences that differ from wild type in only 2 amino acids (mutant 6) or three amino acids (mutant 1) and yet will orient an immune response preferentially toward type 1 (i.e., as indicated by IFN-γ) rather than the type 2 immune response indicated by the presence of IL-5.

The data presented herein provide a positive correlation between peptides encompassing amino acids 184 to 198, 159 to 198, 159 to 174, 171 to 187, and/or 176 to 190 of G protein and the predisposition for pulmonary eosinophilia. Thus, for seronegative populations, the results argue for the construction of a vaccine for RSV that is genetically modified in one or more of the regions of amino acids 184 to 198, 159 to 198, 159 to 174, 171 to 187, or 176 to 190 of G protein. This vaccine would not bias recipients for atypical pulmonary disease, but would retain an ability to protect against subsequent RSV challenge. The alignment of HLA type with reactivity to peptide 19 may provide a more profound understanding of the role of this amino acid sequence in the onset of bronchiolitis, atopy or asthma that is sometimes observed following RSV infection of seronegative infants (Welliver and Welliver, *Pediatrics in Review* 14:134–139 (1993)). Thus, the most favorable RSV vaccine strategy for seronegative populations would consist of components that, while not priming for immunopathological sequelae, achieve a balanced immune response resulting in the stimulation of protective $CD4^+$ and $CD8^+$ cell types. The data presented in FIGS. 4A and 4B identify a number of peptides which stimulate IFN-γ secretion and may play this role (viz: peptides 10, 14, 16 and 18). Similarly, the data suggested a number of peptides (e.g., for donor 100; peptides 2, 4, 9, 15, and 29) which were able to stimulate proliferation of PBMCs and which may be sufficient for protection against RSV challenge in the absence of the sequence occupying peptide 19. Collectively, the data described herein suggest that the region 159–198 of G protein (and subsequences thereof) has the capacity to prime multiple mouse strains for pulmonary eosinophilia, and also demonstrate that immune responses to specific peptides of this region are genetically determined.

The following Examples are offered for the purpose of illustrating the present invention and are not to be construed to limit the scope of this invention. The teachings of all references cited herein are hereby incorporated herein by reference.

EXAMPLES

MATERIALS AND METHODS

Mice

Female BALB/c ($H-2^d$) (Taconic Farms, Inc., Germantown, N.Y.), C57B1/6 ($H-2^b$) (Charles River Laboratories, Boston, Mass.), SJL ($H-2^s$) (Jackson Laboratories, Bar Harbor, ME) and C3H/HeJ (H-2k) (Jackson Laboratories) mice, aged 7–9 weeks, were housed in a facility designated by the American Association for Accreditation of Laboratory Animal Care.

Preparation and Use of Vaccine Antigens:

Viral particles from strain A2 of RSV were produced by infecting HEp-2 cells (ATCC CCL 23) and subsequently clarifying the virus by centrifugation of culture supernatants to remove cell debris. RSV F and G proteins were purified from the A2 strain of RSV that had been grown in Vero cells (ATCC CCL 81). G protein was isolated using immunoaffinity chromatography with the G protein-specific monoclonal antibody L7 (hybridoma deposited as ATCC HB10233) as previously described (Hancock et al., *J. Virol.* 70:7783–7791 (1996)). The resultant G protein was determined, by ELISA and SDS-PAGE, to be >95% pure. For immunizations, each mouse was vaccinated intramuscularly at 0 and 4 weeks with 0.1 ml of PBS containing 1 μg of purified G protein and 20 μg Stimulon™ QS-21 (Aquila Biopharmaceuticals, Inc., Framingham, Mass.) as an adjuvant, unless otherwise stated. F protein was purified by ion-exchange chromatography and 3 μg used in vaccinations adjuvanted with 100 μg aluminum hydroxide (AlOH). For RSV vaccinations and challenges, $1–2\times10^6$ plaque forming units (pfu) of infectious RSV A2 was administered intranasally in a 50 μl volume. An equal volume of HEp-2 cell lysate was utilized as a mock vaccination.

Preparation and Use of Peptide Antigens

A series of synthetic peptides corresponding to overlapping regions of the G protein of RSV were synthesized by Genosys Biotechnologies, Inc. (The Woodlands, Tex.)(FIG. 2). The resultant series encompassed amino acids 48–294 of RSV A2 G protein (Wertz et al., *Proc. Natl. Acad. Sci. USA* 82:4075–4079 (1985)). The purity of the peptides was determined by mass spectometry to be above 90%. Lyophilized peptides were dissolved in sterile water to a concentration of 2 mg/ml and stored at −20° C. Peptides were used at a concentration of 50 μg/ml to stimulate human peripheral blood mononuclear cells (PBMCs) or G protein-primed murine spleen cells in vitro.

Selected peptides were conjugated to maleimide-activated (Partis et al., *J. Prot. Chem.* 2:263–277 (1983)) keyhole limpet hemocyanin (KLH) using an Imject® activated conjugation kit (Pierce Chemical, Rockford, Ill.). Since the mechanism of conjugation was dependent upon a chemical reaction between maleimide groups in KLH and SH groups in the peptide, a cysteine was added to the carboxy-terminus end of peptide 22. The degree to which the various peptides were conjugated was quantitated by determining the loss of thiol groups in the peptide, using Ellman's reagent (Pierce Chemical). The extent of conjugation (typically 50–80 μg peptide per mg of KLH) seen in these reactions compared favorably with that previously seen for the attachment of peptides to KLH by this technique (Tsao et al., *Anal. Biochemistry* 197:137–142 (1991)). For study of the induction of eosinophilia by various peptides, 250 μg of KLH conjugated to the respective peptides were adjuvanted with 20 μg Stimulon™ QS-21 in 0.1 ml of PBS and used to immunize each mouse, intramuscularly, at 0 and 4 weeks. Two weeks post secondary vaccination, mice were challenged with $1–2\times10^6$ PFU of infectious RSV A2, administered intranasally in a 50 μl volume (Hancock et al., *J. Virol* 70:7783–7791 (1996)). Seven days later, mice were sacrificed by cervical dislocation and bronchoalveolar lavage (BAL) was performed.

Titration of Infectious RSV:

Supernatants derived from the homogenized lungs of RSV-infected mice were serially diluted and permitted to infect monolayers of HEp-2 cells. After a 2-hour incubation, the inoculum was aspirated and each well was overlayed with 1% Sephadex G-75 in media. After a further 3 day incubation, the gel overlay was removed and the wells were fixed in 80% methanol. RSV plaques were identified using a monoclonal antibody to RSV G protein and a secondary mAb of goat anti-mouse conjugated to horseradish peroxidase. Color was developed by addition of the substrate, 0.05% 4-chloronaphthol/0.09% hydrogen peroxide in phosphate buffered saline (PBS). RSV plaque forming units (pfu) were enumerated and the titers expressed as pfu per gram of lung tissue.

BALB/c mice were primed intramuscularly with one of several vaccines composed of the native fusion (F) and/or attachment (G) proteins purified from the A2 strain of RSV. Three groups of mice were primed with either 3,000, 300, or 30 ng F protein/dose. Three separate groups of mice were primed with 1,000, 100, or 10 ng G protein/dose. Also 3 groups of mice were primed with a combination vaccine containing 3,000+1,000; 300+100: or 30+10 ng F and G protein, respectively. All vaccines were formulated with aluminum hydroxide (AlOH, 100 μg/dose). Control mice were either infected with the A2 strain of RSV or received an intramuscular injection of PBS/AlOH. Four weeks after primary immunization all mice were challenged with the A2 strain of RSV. Four days later the mice were sacrificed and the pulmonary tissues were processed for the quantitation of infectious virus (Table).

TABLE

Determination of RSV titers in Mouse Lung

| ANTIGEN (ng) | GMT RSV[a] |
|---|---|
| F(3000) + G(1000) | <1.6 ± 0.2 |
| F(300) + G(100) | <2.1 ± 0.7 |
| F(30) + G(10) | <2.8 ± 0.9[b] |
| F(3000) | <2.1 ± 0.5 |
| F(300) | <2.5 ± 1.0 |
| F(30) | 4.1 ± 0.8 |
| G(1000) | 3.5 ± 0.5 |
| G(100) | 4.7 ± 0.2 |
| G(10) | 4.7 ± 0.2 |
| PBS | 5.1 ± 0.2 |
| RSV | <1.6 ± 0.1 |

[a]GMT is the geometric means titer ($log_{10}$) ± 1 standard deviation of RSV per gram of pulmonary tissue. The GMT RSV was determined 4 days after intranasal challenge.
[b]$P < 0.05$ vs. groups vaccinated with F (30) alone, G (10) alone, or PBS.

Bronchoalveolar Lavages:

Bronchoalveolar lavages (BAL) were performed by infusing into the trachea, and withdrawing, for a minimum of five repetitions, a solution containing 1 ml of ice-cold 12 mM Lidocaine HCl in RPMI (Hancock et al., *Vaccine* 13:391–400 (1995)). The BAL suspension was then centrifuged to pellet the cells. Leukocytes were quantified by staining an aliquot of the cells with 0.2% trypan blue in PBS. Subsequently, cells were cytospun onto glass slides, fixed and stained with Diff-Quik (Dade International Inc., Miami, Fla.)). Individual leukocyte populations were enumerated by analyzing a minimum of 400 cells per slide. The results are expressed as mean percent (+SD) of five mice per group.

In Vivo Depletion of T Cell Subsets

Monoclonal antibodies (mAbs) to murine CD4, GK1.5 (ATCC TIB 207) and murine CD8, 53–6.72 (ATCC TIB 105) were purified from hybridoma culture supernatants over a recombinant protein G column (Pharmacia, Piscataway, N.J.). As a control, purified rat IgG was purchased from Calbiochem (San Diego, Calif.). MAbs were administered at 14 and 20 days post final immunization in doses of 750 μg and 250 μg per mouse, respectively. Mice were subsequently challenged with live RSV and pulmonary eosinophilia quantitated by analysis of BAL-derived cells 7 days thereafter. Flow cytometry was performed on a FACScan (Becton Dickinson, Mountain View, Calif.) to assess the effectiveness of the depletion regime. Standard flow cytometric techniques were used using PE anti-mouse CD4 (L3T4) and FITC anti-mouse CD8 (Ly-2) purchased from Pharmingen (San Diego, Calif.).

In Vitro Expansion of Splenic Immunocytes:

Spleens were isolated from groups of five mice two weeks post-secondary vaccination with native G protein and Stimulon™ QS-21 and were converted to single cell suspensions as previously described (Hancock et al., *J. Virol.* 70:7783–7791 (1996)). Erythrocytes were removed using ammonium chloride lysis and the resultant spleen cells quantified by trypan blue exclusion. Cells were cultured, in triplicate, in 96-well flat bottomed plates at a concentration of $2.5\times10^5$ cells per well in a medium containing RPMI 1640 supplemented with 2 mM glutamine; 100 U of penicillin and 50 μg streptomycin per ml; $5\times10^{-4}$ M β-mercaptoethanol; 10 mM HEPES; 1% normal mouse serum (Biocell Labs, Inc., Rancho Dominguez, Calif.). Peptide antigens were added to the culture medium at a concentration of 50 μg per ml. As controls, purified G protein, diphtheria toxoid cross-reactive protein ($CRM_{197}$) and Concanavalin A (ConA) were added at final concentrations of 0.5 μg/ml, 10 μg/ml and 1 μg/ml, respectively. After 4 days in culture at 37° C. and 5% $CO_2$, cells were pulsed with 1 μCi of $^3$H-thymidine for a further 18 hours. Cells were subsequently harvested and $^3$H-thymidine incorporated into DNA was determined by liquid scintillation counting.

Heparinized human blood was collected from normal adult donors and separated using Ficoll-Hypaque (Pharmacia, Piscataway, N.J.) centrifugation. Cells were cultured with peptides as described above in RPMI 1640 medium containing 10% $AB^-$ serum (Biocell). As controls, cells were cultured with $CRM_{197}$ (30 μg/ml), PHA (5 μg/ml) or in medium alone.

Cytokine Assays:

Pooled supernatants from triplicate wells were assayed for IFN-γ and IL-5 by antigen-capture ELISA. Briefly, maxisorb plates (Nunc) were coated with 50 μl of carbonate-bicarbonate buffer (pH 9.6) containing either R4-6A2 (3 μg/ml) or TRFK.5 (2.5 μg/ml) monoclonal antibodies for the capture of IFN-γ and IL-5, respectively. Non-specific binding sites were blocked using Tris-buffered saline containing 5% FBS and 10% milk powder (wt/vol). Culture supernatants were added to the wells in duplicate and allowed to incubate at room temperature for 2 hours. To detect bound cytokine, biotinylated antibodies XMG1.2 (IFN-γ) and TRFK.4 (IL-5) were used at concentrations of 1 μg/ml and 2 μg/ml, respectively. All four monoclonal antibodies used in the cytokine assays were obtained from Pharmingen (San Diego, Calif.). Cytokines were quantitated using streptavidin-alkaline phosphatase with a substrate system consisting of NADP, diaphorase, alcohol dehydrogenase and INT violet. Substrate color development proceeded by adding 0.3 M sulfuric acid and optical density determined at 490 nm ($OD_{490}$) on a Dynatech (Chantilly, Va.) ELISA reader. Standard curves were generated for each cytokine using recombinant IFN-γ (Genzyme, Cambridge, Mass.) and IL-5 (Pharmingen, San Diego, Calif.) in order to ensure linearity. Data are presented as mean $OD_{490}$ for each antigen.

Induction of Pulmonary Eosinophilia:

Mice, aged 7 to 9 weeks, (5 mice per group) were vaccinated intramuscularly at 0 and 4 weeks with 0.1 ml of PBS adjuvanted with 20 μg Stimulon™ QS-21 and containing either 1 μg of purified G protein; 250 μg KLH; 250 μg KLH conjugated to peptides 19 or 22 or 250 μg free peptide 19 or 22. Peptides were conjugated to maleimide-activated KLH using an Imject® activated conjugation kit (product no. 77111) purchased from Pierce Chemical, Rockford, Ill. Typically, for each conjugation reaction, 80–100 μg of peptide was bound to 1 mg of KLH. Thus, since each mouse received 250 μg KLH per vaccination, this corresponded to 20–25 μg of the relevant peptide. Two weeks post-secondary vaccination, mice were challenged with $1–2\times10^6$ PFU of infectious RSV A2 by intranasal instillation in a 50 μl volume. Seven days later mice were sacrificed by cervical dislocation and bronchoalveolar lavage was performed. Cells were cytospun onto glass slides, fixed and stained with Diff-Quik (Dade Diagnostics). The relative proportion of eosinophils, as a function of total white cells, was enumerated by analyzing a minimum of 400 cells per slide. The results are expressed as mean percent (+SD) of five mice per group.

Statistical Analyses

Significant differences between groups were determined by the Tukey-Kramer HSD multiple comparisons test using JMP® statistical discovery software (SAS Institute Inc., Cary, N.C).

RESULTS

The immune responses elicited by native G protein and a series of overlapping peptides (shown in FIG. 2) extending from amino acids 48 to 294 of G protein have been characterized as a result of work described herein. Amino acid 48 corresponds to the second translational start codon of RSV G protein. BALB/c mice that received an intramuscular (IM) vaccination of native G protein at 0 and 4 weeks exhibited maximal bronchoalveolar lavage (BAL) eosinophilia (65% of total white cells) at 7 days post-intranasal (IN) challenge with live RSV. In contrast, the BAL fluids of mice vaccinated by experimental infection or experiencing primary infection contained less than 2% eosinophils (FIG. 1B).

Figure 3:
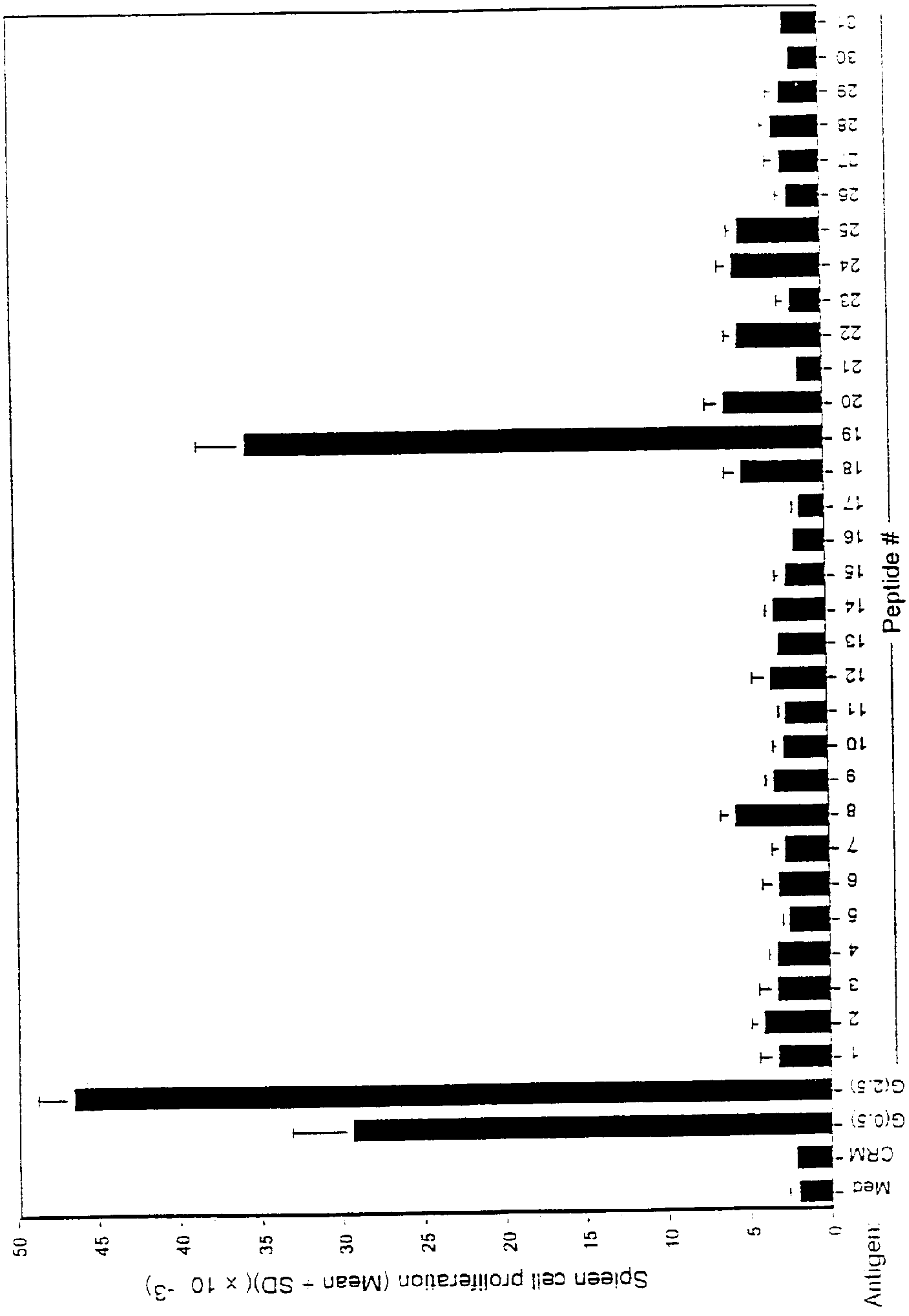
FIG. 3 is a bar graph illustrating stimulation of G protein-primed splenocytes from BALB/c mice with G protein-derived peptides. BALB/c mice were vaccinated at 0 and 4 weeks with 1 μg G protein adjuvanted with Stimulon™ QS-21. Two weeks post-secondary vaccination, splenocytes from 5 mice were isolated, pooled and cultured in the presence of antigen for 4 days. Each synthetic peptide was supplied at a concentration of 50 μg/ml. Native G protein was added at concentrations of 0.5 and 2.5 μg/ml. Concanavalin A (ConA) stimulation of splenocytes resulted in a mean cpm of 94,746±8005. As controls, cultures were also stimulated with medium alone (Med) or $CRM_{197}$ (CRM). Data are presented as the mean (±SD) of triplicate wells. The experiment is representative of five independent experiments, each of which showed qualitatively similar results.

In vitro stimulation assays of spleen cells from G protein-vaccinated BALB/c mice showed a dominant proliferative response to a peptide encompassing amino acids 184–198 of G protein (FIG. 3). Proliferation was 16-fold above background levels and far exceeded that attained by other G protein-derived peptides. In addition, the magnitude of the response to peptide 19 was comparable to that attained with purified native G protein. The data therefore indicate that the ability of RSV G protein to stimulate proliferation of primed splenocytes from BALB/c mice is entirely contained within the segment of protein occupying amino acids 184–198.

Figure 4A:
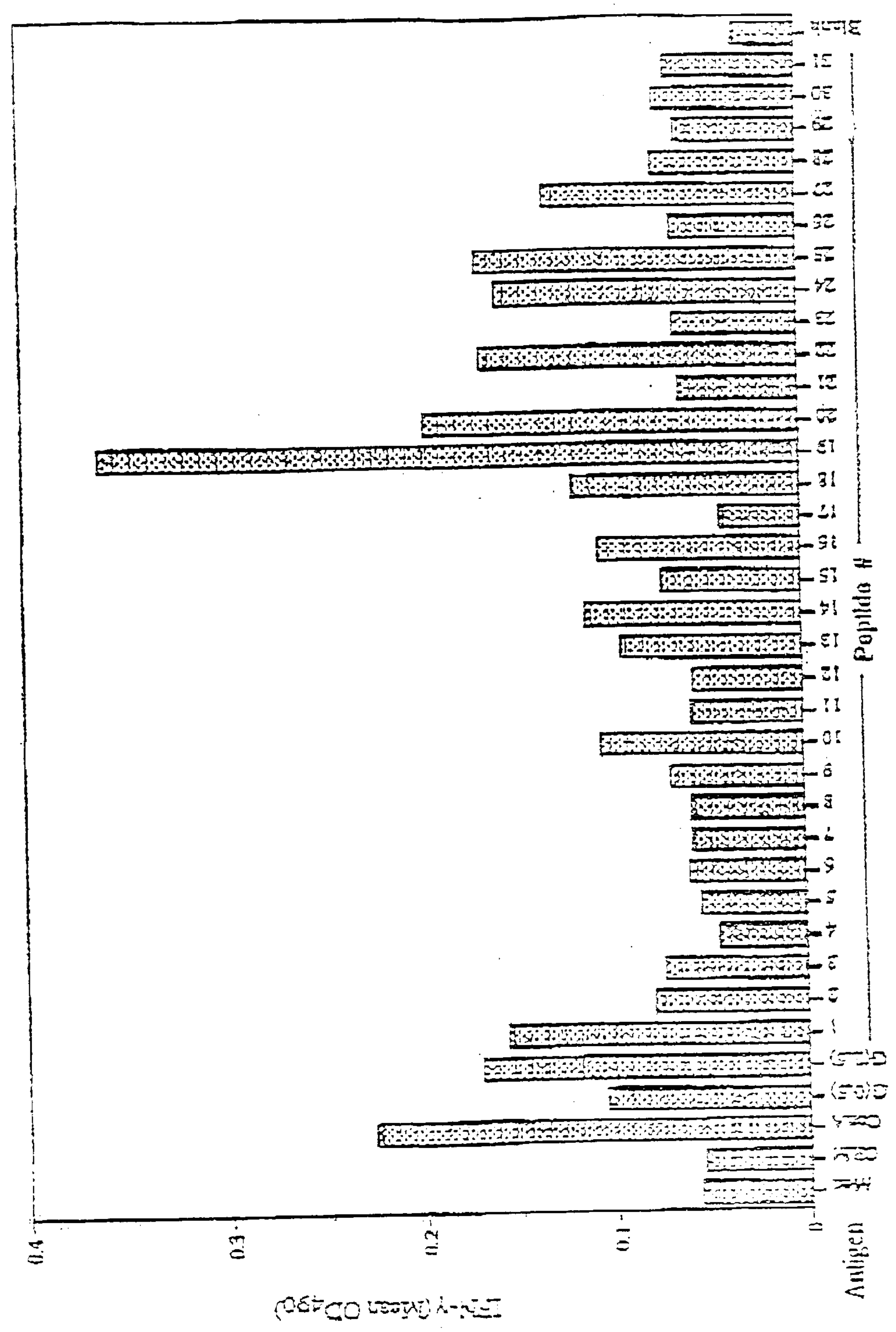
FIGS. 4A and 4B are bar graphs showing an analysis of peptide-induced cytokines (IFN-γ and IL-5) in culture supernatants. Splenocytes from BALB/c mice vaccinated with native G protein and Stimulon™ QS-21 were cultured with the peptide antigens as described in the description of FIG. 3. After 4 days of culture, 100 μl of supernatant was pooled from triplicate wells and subsequently assayed for IFN-γ (FIG. 4A) and IL-5 (FIG. 4B) by antigen capture ELISA. The data are presented as the mean $OD_{490}$ of duplicate cytokine analyses.
Figure 4B:
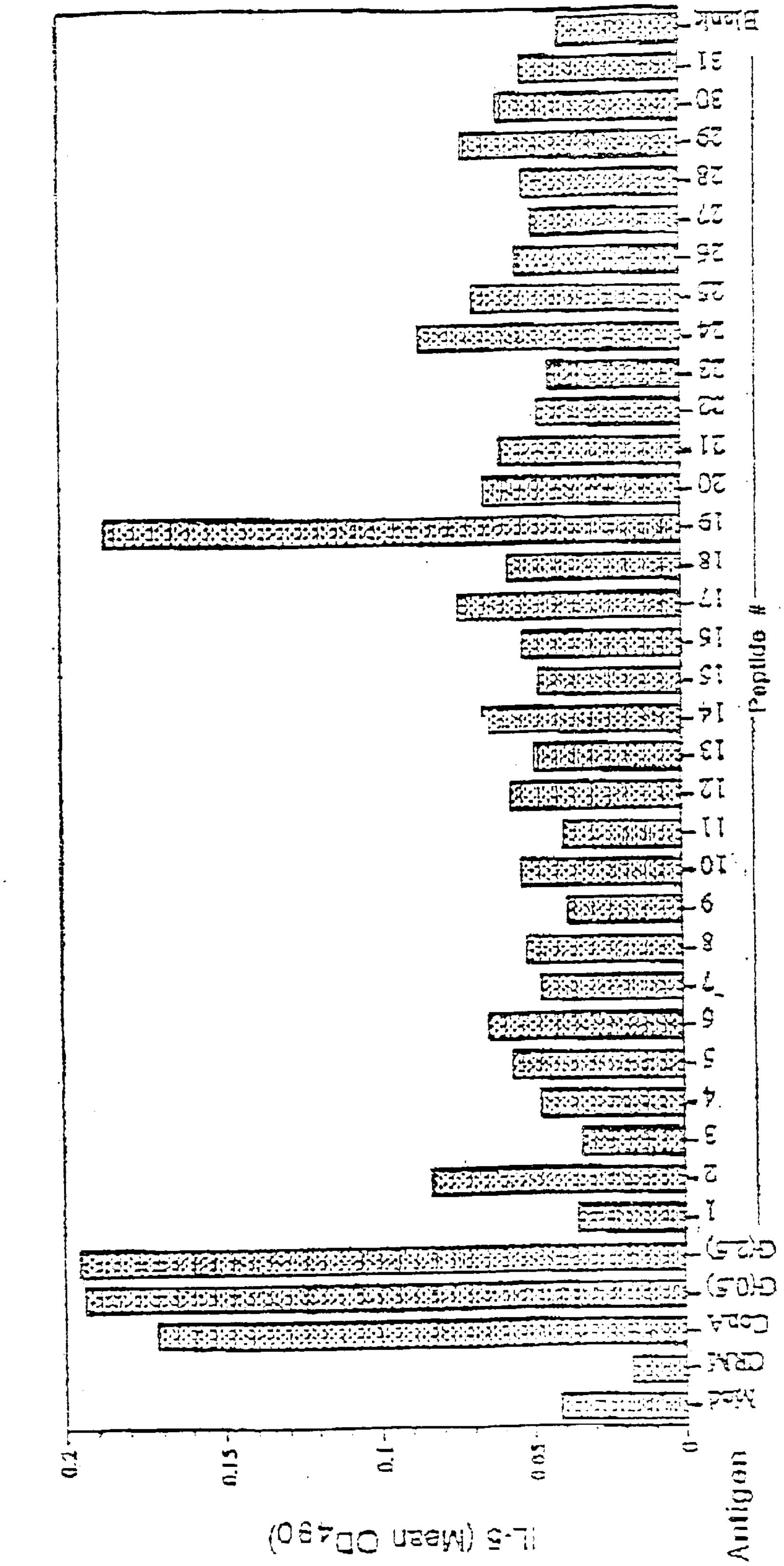

Analysis of culture supernatants for cytokines associated with helper T cell subsets indicated that the highest levels of IFN-γ and IL-5 were observed after stimulation with peptide 19. Moreover, the levels were equivalent to, or greater than, those obtained after restimulation with native G protein (FIGS. 4A and 4B). This data indicates that a region spanning amino acids 184–198 contains the dominant epitope(s) in RSV G protein recognized by T cells in BALB/c mice.

Preliminary studies demonstrated that the pulmonary eosinophilia in BALs of BALB/c mice vaccinated with G protein peaked at 65±5.4%, 7 days post-challenge. To confirm the direct role of peptide 19 in priming for pulmonary eosinophilia in mice, peptide 19 was compared to peptide 22. The latter peptide appeared to stimulate IFN-γ production, without the stimulation of IL-5 (FIGS. 4A and 4B).

Figure 5:
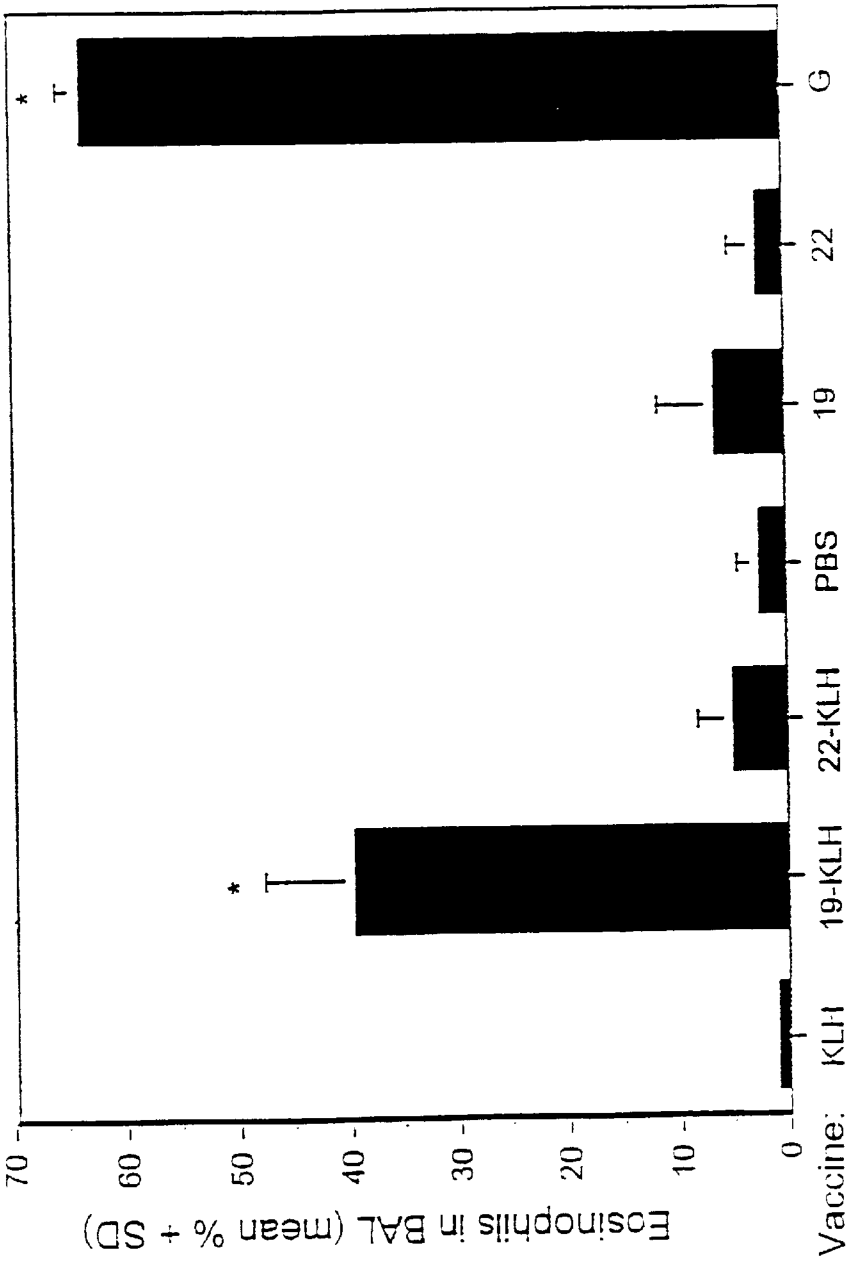
FIG. 5 is a bar graph showing the specific induction of pulmonary eosinophilia in BALB/c mice by peptide 19. Significant differences (*) are shown for G protein or 19-KLH vaccinated mice compared to control mice that received either PBS or KLH. The data are representative of three experiments in which similar results were obtained.

To ensure sufficient immunogenicity, the peptides were conjugated to maleimide-activated KLH. Statistically significant pulmonary eosinophilia was observed in mice that had been primed with peptide 19-KLH (39.5±8.0%) or G protein (63±1.9%) compared to mice vaccinated with adjuvant alone (2.5±2.0%) (FIG. 5). In contrast, the level of eosinophilia associated with peptide 22-KLH (4.9±3.3%) was at background levels, despite data showing that peptide 22 was immunogenic. Two weeks post final vaccination, the geometric mean anti-RSV G protein IgG titers of mice vaccinated with peptide 19-KLH or peptide 22-KLH were 1517 and 5611, respectively. Thus, although humoral immune responses were generated to each of the peptide-conjugates, the induction of aberrant eosinophilia was limited to those mice that received peptide 19. Immunization with unconjugated peptides 19 or 22 did not elicit a detectable humoral immune response and yielded relative percentages of eosinophilia (6.5±5.2% and 2.5±2.5, respectively) that were not significantly different from PBS/Stimulon™ QS-21 controls.

In order to assess peptide 19 as the causative agent of pulmonary eosinophilia, mutants of peptide 19 with amino acid substitutions at the critical 1, 4, 6 and 9 anchor regions of the MHC class II binding site were assessed. These mutations abrogated the ability to predispose mice for pulmonary eosinophilia (FIG. 6). In assoication with FIG. 5, this data indicates a direct relationship between the amino acid sequence of peptide 19 and the induction of pumonary eosinophilia in mice upon subsequent challenge.

To determine whether the peptide 19-KLH associated eosinophilia was mediated by $CD4^+$ cells, a series of depletion experiments were performed using mAbs to CD4 or CD8 surface molecules. FACS analysis was performed on gated populations of lymphocytes from the spleens of vaccinated mice 7 days post-challenge (FIG. 8).

The depletion of $CD4^+$ cells resulted in a significant reduction in BAL eosinophilia in mice vaccinated with either G/Stimulon™ QS-21 or peptide 19-KLH/Stimulon™ QS-21 (FIG. 8). Specifically, treatment with anti-CD4 mAb significantly reduced pulmonary eosinophilia from 67.2±8.5% and 29.6±13.3% to 8.1±4.7% and 0.75±0.6%, respectively. The corresponding effect of anti-CD8 mAb treatment had minimal impact on the induction of eosinophilia, since levels persisted at 63.8±6.4% and 32.8±10.3% for G and peptide 19-KLH vaccinated mice, respectively. As shown in FIG. 8, only 0.7% eosinophilia was observed in the BAL of mice experimentally infected with RSV. Thus, the data demonstrate that $CD4^+$ cells are required for the pulmonary eosinophilic response seen in G protein or peptide 19 immunized BALB/c mice upon challenge.

Figure 7:
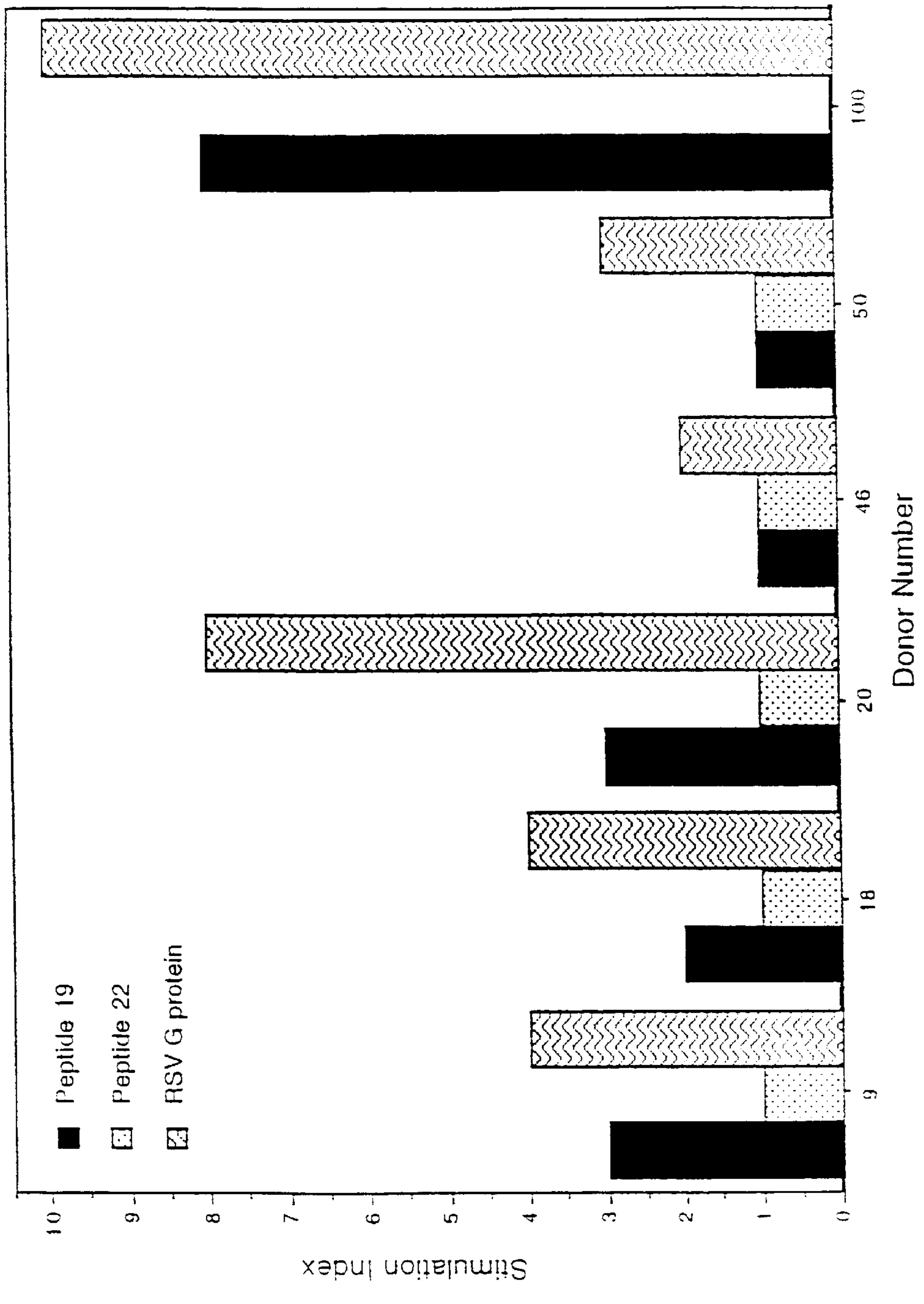
FIG. 7 is a bar graph showing the proliferative responses of human PBMCs to G protein-derived peptides. PBMCs from 6 out of 43 donors that showed reactivity to RSV G protein were assayed for proliferation by culture in the presence of synthetic peptides 19 and 22. Each peptide was supplied at a concentration of 50 μg/ml. Purified G protein was added at a concentration of 3 μg/ml. PHA stimulation of PBMCs from all donors ranged from 22,945 to 55,619 cpm. PBMCs were also cultured in media alone and stimulation index calculated. Data are presented as the mean stimulation index obtained from triplicate cultures.

The peripheral blood mononuclear cells from a panel of donors were tested for reactivity to purified G protein to identify individuals which had undergone a recent infection. Subsequently, the cells from six donors that showed a proliferative response to G protein were cultured in the presence of the synthetic peptides described in FIG. 2 (FIG. 7). A strong proliferative response to peptide 19 was observed for donor 100 (mean stimulation index, 8.5). In addition, proliferative responses to peptide 19 were apparent in donors 9 and 20 with mean stimulation indices of 3-fold in each case.

Figure 9:
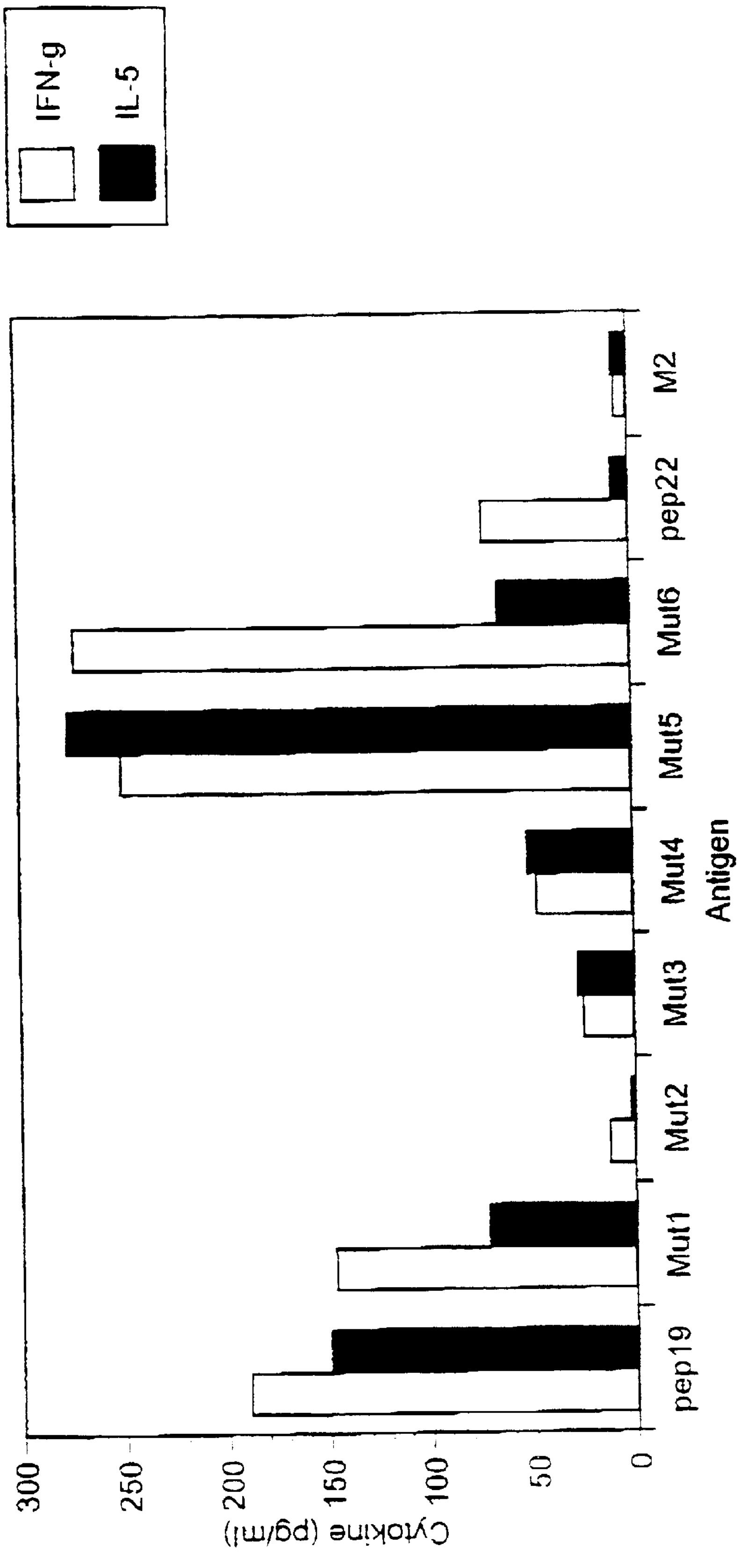
FIG. 9 is a graph showing the ability of particular peptides to orient an immune response preferentially toward type 1 (as indicated by IFN-γ) as opposed to type 2 (as indicated by IL-5). Peptide 19 (AICKRIPNKKPGKKT; SEQ ID NO: 19), peptide 19 mutant 1 (AICGRGPNGKPGKKT; SEQ ID NO: 32), peptide 19 mutant 2 (AGCGRGPGGKPGKGT; SEQ ID NO: 33), peptide 19 mutant 3 (AICGRGPNKKPGKKT; SEQ ID NO: 34), peptide 19 mutant 4 (AICGRIPNKKPGKKT; SEQ ID NO: 35), peptide 19 mutant 5 (AGCKRIPNKKPGKKT; SEQ ID NO: 36), peptide 19 mutant 6 (AGCKRIPNKGPGKKT; SEQ ID NO: 37), and peptide 22 (LKTTKKDPKPQTTKS; SEQ ID NO: 22) were utilized. Spleens were isolated from groups of five mice two weeks post-secondary vaccination with peptide 19-KLH/QS-21 and were converted to single cell suspensions. Cells were cultured, in triplicate, in 96-well flat-bottomed plates at a concentration of 2.5×$10^5$ cells per well in a medium consisting of RPMI 1640 supplemented with 2 mM glutamine; 100 U of penicillin and 50 μg streptomycin per ml; 5×$10^{-4}$ Mβ mercaptoethanol; 10 mM HEPES; 1% normal mouse serum (Biocell Labs, Inc., Rancho Dominguez, Calif.). Peptide antigens described above were added to the culture medium at a concentration of 50 μg per ml. As a negative control, a non-specific peptide from the M2 protein of RSV (M2) was added at final concentration of 50 $\mu$g per ml. After 3 days in culture at 37° C. and 5% $CO_2$, cell supernatants were isolated and analyzed for IL-5 and IFN-γ by cytokine ELISA.

The data presented in FIG. 9 suggest that a more selective mutational analysis can result in sequences that differ from wild type in only 2 amino acids (mutant 6) or three amino acids (mutant 1) and yet will orient an immune response preferentially toward type 1 (i.e., as indicated by IFN-γ) rather than the type 2 immune response indicated by the presence of IL-5. Moreover, the data presented in FIG. 6 additionally show that such mutations (specifically regarding mutant 1) do not predispose BALB/c mice for pulmonary eosinophilia. Additional alterations can be similarly assessed as described herein to determine whether they have a similar immunological effect and/or a similar effect on predisposition for pulmonary eosinophilia.

FIGS. 10A–10C and 11A–11C show that host genetic determinants regulate the immune response to the attachment (G) protein of respiratory syncytial virus in mice. Immunization with natural G protein purified from RSV has been associated with the onset of pulmonary eosinophilia after challenge, and the production of interleukin 5 (IL-5), a Th2 type cytokine. As described herein, a peptide encompassing amino acids 184 to 198 of natural G protein is associated with priming BALB/c mice for $CD4^+$ T cell-mediated pulmonary eosinophilia. Further assessment was performed to identify the genetic components that influence the qualitative nature of the immune response to natural G protein in mice. The genetic background of mice was found to be important for the generation of pulmonary eosinophilia at the level of peptide 184–198 but not at the level of G protein. Immunization with purified natural G protein primed C57BL/6 (H-$2^b$), SJL (H-$2^s$), and C3H/HeJ (H-$2^k$)

mice, as well as BALB/c (H-$2^d$) mice, for significant lung eosinophilia (>50%) upon subsequent challenge (FIG. 10A). Whereas vaccination with peptide 184–198 was associated with significant eosinophilia in BABL/c mice (27%), comparatively less eosinophilia was observed in C57BL/6 (5%), C3H/HeJ (2%) or SJL (2%) mice (FIG. 10B). In accordance with a MHC influence upon immune responsiveness to peptide 184–198, in vitro stimulation assays of primed spleen cells showed a varied proliferative response to overlapping peptides of G protein (FIGS. 11A–11C). BALB/c splenocytes (FIG. 3) were unique in displaying maximal proliferation to peptide 184–198 of G protein, whereas splenocytes from C57BL/6, SJL and C3H/HeJ mice responded maximally to peptides encompassing amino acids 171–187, 176–190 and 159–174, respectively (FIGS. 10A, 10B and 10C, respectively). Peripheral blood cells from donors that show a proliferative response to G protein can be cultured in the presence of synthetic peptides 15, 17 or 18 as described herein to identify peptides which are able to elicit a proliferative response to these peptides in a percentage of individuals. Such studies allow a determination of the appropriate vaccine or immunogenic composition for a particular subset of vertebrates.

EQUIVALENTS

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. An isolated altered G protein or polypeptide of RSV, wherein the alteration is in one or more regions selected from the group consisting of the region from amino acid 159 to amino acid 198, the region from amino acid 159 to amino acid 174 as set out in SEQ ID NO: 15, the region from amino acid 171 to amino acid 187 as set out in SEQ ID NO: 17, the region from amino acid 176 to amino acid 190 as set out in SEQ ID NO: 18, and the region from amino acid 184 to amino acid 198 as set out in SEQ ID NO: 19, and where said isolated, altered G protein or polypeptide retains immunogenicity, and which isolated, altered G protein or polypeptide, when incorporated into an immunogenic composition and administered to a vertebrate, does not induce enhanced disease upon subsequent infection of the vertebrate with RSV.

2. The isolated, altered G protein or polypeptide according to claim 1, wherein the enhanced disease is atypical pulmonary inflammation.

3. The isolated, altered G protein or polypeptide according to claim 2, wherein the atypical pulmonary inflammation is pulmonary eosinophilia.

4. The isolated, altered G protein or polypeptide according to claim 1, wherein the alteration results in inhibition of priming for IL-5 secretion by the isolated, altered G protein or polypeptide relative to wild type G Protein.

5. The isolated, altered G protein of polypeptide according to claim 1, wherein the alteration results in enhancement of priming for IFN-γ secretion by the isolated, altered G protein or polypeptide relative to wild type G protein.

6. The isolated altered G protein or polypeptide according to claim 1, wherein said alteration is in the region from amino acid 184 to amino acid 198.

7. An immunogenic composition comprising a physiologically acceptable medium and an isolated altered G protein or polypeptide of RSV, wherein the alteration is in one or more regions selected from the group consisting of the region from amino acid 159 to amino acid 198, the region from amino acid 159 to amino acid 174 as set out in SEQ ID NO: 15, the region from amino acid 171 to amino acid 187 as set out in SEQ ID NO; 17, the region from amino acid 176 to amino acid 190 as set out in SEQ ID NO: 18, and the region from amino acid 184 to amino acid 198 as set out in SEQ ID NO: 19, and where said altered G protein or polypeptide retains immunogenicity, and which altered G protein or polypeptide, when incorporated into an immunogenic composition and administered to a vertebrate, does not induce enhanced disease upon subsequent infection of the vertebrate with RSV.

8. The immunogenic composition according to claim 7, wherein the immunogenic composition results in inhibition of priming for IL-5 secretion relative to an immunogenic composition comprising wild type G protein.

9. The immunogenic composition according to claim 7, wherein the immunogenic composition results in enhancement of priming for IFN-γ secretion relative to an immunogenic composition comprising wild type G protein.

10. An immunogenic composition comprising a physiologically acceptable medium, isolated F protein of RSV and an isolated altered G protein or polypeptide of RSV, wherein the alteration is in one or more regions selected from the group consisting of the region from amino acid 159 to amino acid 198, the region from amino acid 159 to amino acid 174 as set out in SEQ ID NO: 15, the region from amino acid 171 to amino acid 187 as set out in SEQ ID NO: 17, the region from amino acid 176 to amino acid 190 as set out in SEQ ID NO: 18, and the region from amino acid 184 to amino acid 198 as set out in SEQ ID NO: 19, and where said isolated, altered G protein or polypeptide retains immunogenicity and which isolated, altered G protein or polypeptide, when incorporated into an immunogenic composition and administered to a vertebrate does not induce enhanced disease upon subsequent infection of the vertebrate with RSV.

11. The immunogenic composition according to claim 10, wherein the immunogenic composition results in inhibition of priming for IL-5 secretion relative to wild-type G protein.

12. The immunogenic composition according to claim 10, wherein the immunogenic composition results in enhancement of priming for IFN-γ secretion relative to wild-type G protein.

13. The immunogenic composition according to claim 10, wherein the alteration is in the region from amino acid 184 to amino acid 198 of the G protein.

14. A method of inhibiting induction of enhanced disease after immunization and subsequent infection of a vertebrate with RSV, comprising administering an isolated altered RSV G protein or polypeptide, wherein the alteration is in one or more regions selected from the group consisting of the region from amino acid 159 to amino acid 198, the region from amino acid 159 to amino acid 174 as set out in SEQ ID NO: 15, the region from amino acid 171 to amino acid 187 as set out in SEQ ID NO: 17, the region from amino acid 176 to amino acid 190 as set out in SEQ ID NO: 18, and the region from amino acid 184 to amino acid 198 as set out in SEQ ID NO: 19, and where said isolated, altered G protein or polypeptide retains immunogenicity, and which isolated, altered G protein or polypeptide, when incorporated into an immunogenic composition and administered to a vertebrate, provides protection without inducing enhanced disease upon subsequent infection of the vertebrate with RSV.

15. A method of immunizing a vertebrate against RSV, comprising administering to the vertebrate a composition comprising an immunologically effective amount of an isolated, altered G protein or polypeptide of RSV, wherein the alteration is in one or more regions selected from the group consisting of the region from amino acid 159 to amino acid 198, the region from amino acid 159 to amino acid 174 as set out in SEQ ID NO: 15, the region from amino acid 171 to amino acid 187 as set out in SEQ ID NO: 17, the region from amino acid 176 to amino acid 190 as set out in SEQ ID NO: 18, and the region from amino acid 184 to amino acid 198 as set out in SEQ ID NO: 19, and where said isolated, altered G protein or polypeptide retains immunogenicity, and which isolated, altered G protein or polypeptide, when incorporated into an immunogenic composition and administered to a vertebrate, does not induce enhanced disease upon subsequent infection of the vertebrate with RSV.

16. The method according to claim 15, wherein the composition further comprises an immunologically effective amount of isolated RSV F protein.

17. The method according to claim 15, wherein the vertebrate is a seronegative human.

18. An isolated, altered G protein or polypeptide of RSV which retains immunogenicity and which, when incorporated into an immunogenic composition and administered to a vertebrate, does not induce enhanced disease upon subsequent infection of the vertebrate with RSV, said protein or polypeptide having an amino acid sequence selected from the group consisting of SEQ ID NO: 32, SEQ ID NO: 33 and SEQ ID NO: 37.

19. An immunogenic composition comprising a physiologically acceptable medium and an altered G protein or polypeptide of RSV which retains immunogenicity and which, when incorporated into an immunogenic composition and administered to a vertebrate, does not induce enhanced disease upon subsequent infection of the vertebrate with RSV, said protein or polypeptide having amino acid sequence selected from the group consisting of SEQ ID NO: 32, SEQ ID NO: 33 and SEQ ID NO: 37.

* * * * *